(12) United States Patent
Kimura et al.

(10) Patent No.: US 10,312,452 B2
(45) Date of Patent: Jun. 4, 2019

(54) AROMATIC AMINE DERIVATIVE AND ORGANIC ELECTROLUMINESCENCE DEVICE UTILIZING THE SAME

(71) Applicants: Makoto Kimura, Nagoya (JP); Chishio Hosokawa, Sodegaura (JP); Masakazu Funahashi, Sodegaura (JP)

(72) Inventors: Makoto Kimura, Nagoya (JP); Chishio Hosokawa, Sodegaura (JP); Masakazu Funahashi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 145 days.

(21) Appl. No.: 14/269,658

(22) Filed: May 5, 2014

(65) Prior Publication Data

US 2014/0239283 A1    Aug. 28, 2014

Related U.S. Application Data

(63) Continuation of application No. 11/909,003, filed as application No. PCT/JP2006/304259 on Mar. 6, 2006, now abandoned.

(30) Foreign Application Priority Data

Mar. 18, 2005  (JP) ................................. 2005-078599

(51) Int. Cl.

| | | |
|---|---|---|
| C09B 57/00 | (2006.01) | |
| C09K 11/06 | (2006.01) | |
| H01L 51/00 | (2006.01) | |
| H01L 51/50 | (2006.01) | |
| H05B 33/14 | (2006.01) | |
| C07C 211/58 | (2006.01) | |
| C07C 211/61 | (2006.01) | |
| C07C 217/92 | (2006.01) | |

(52) U.S. Cl.
CPC ........ *H01L 51/0058* (2013.01); *C07C 211/58* (2013.01); *C07C 211/61* (2013.01); *C07C 217/92* (2013.01); *C09B 57/00* (2013.01); *C09B 57/008* (2013.01); *C09K 11/06* (2013.01); *H01L 51/006* (2013.01); *H01L 51/0059* (2013.01); *H01L 51/50* (2013.01); *H05B 33/14* (2013.01); *C09K 2211/1014* (2013.01); *H01L 51/0035* (2013.01); *H01L 51/0039* (2013.01); *H01L 51/0081* (2013.01); *H01L 51/5012* (2013.01); *H01L 2251/308* (2013.01)

(58) Field of Classification Search
CPC ... H01L 51/0058; H01L 51/006; H01L 51/50; C09K 11/06

See application file for complete search history.

(56) References Cited

U.S. PATENT DOCUMENTS

| 5,853,934 | A | 12/1998 | Watanabe et al. | |
|---|---|---|---|---|
| 6,479,172 | B2* | 11/2002 | Hu | C07C 13/567 252/301.16 |
| 6,743,948 | B1 | 6/2004 | Hosokawa et al. | |
| 7,348,072 | B2* | 3/2008 | Park | C08G 61/02 257/40 |
| 8,334,058 | B2* | 12/2012 | Heil | C07C 17/12 257/40 |
| 8,852,756 | B2* | 10/2014 | Vestweber | C07C 13/62 252/301.16 |
| 2003/0118866 | A1* | 6/2003 | Oh | H01L 51/0058 428/690 |
| 2003/0219625 | A1* | 11/2003 | Wolk | C09K 11/06 428/690 |
| 2004/0214036 | A1* | 10/2004 | Bentsen | C07D 271/107 428/690 |
| 2005/0059730 | A1 | 3/2005 | Ohba et al. | |
| 2005/0236974 | A1 | 10/2005 | Suzuki et al. | |
| 2006/0058494 | A1 | 3/2006 | Busing et al. | |
| 2008/0145708 | A1* | 6/2008 | Heil | C07C 17/12 428/704 |
| 2008/0220285 | A1* | 9/2008 | Vestweber | C07C 13/62 428/690 |
| 2009/0179551 | A1* | 7/2009 | Kwon | C09K 11/06 313/504 |

(Continued)

FOREIGN PATENT DOCUMENTS

| EP | 0 926 216 A1 | 6/1999 |
|---|---|---|
| JP | 10-90920 | 4/1998 |
| JP | 11-144875 | 5/1999 |

(Continued)

OTHER PUBLICATIONS

Organic Letters, (2005), vol. 7, No. 5, pp. 795-797.*

(Continued)

*Primary Examiner* — Dawn L Garrett
(74) *Attorney, Agent, or Firm* — Oblon, McClelland, Maier & Neustadt, L.L.P.

(57) ABSTRACT

Provided is a novel aromatic amine derivative with specified structure. Also provided is an organic electroluminescence device having one or more organic thin-film layers including at least a luminescent layer interposed between a cathode and an anode, in which at least one of the organic thin-film layers contains the above aromatic amine derivative alone or as a component of mixture. As a result, there is provided an organic electroluminescence device that has high emission luminance and high heat resistance, excelling in high-temperature storage ability and has long life, and provided an aromatic amine derivative for realizing the organic electroluminescence device.

19 Claims, 1 Drawing Sheet

(56) References Cited

U.S. PATENT DOCUMENTS

2011/0114930 A1* 5/2011 Kim ...................... H01L 51/006
257/40

FOREIGN PATENT DOCUMENTS

| JP | 11-162642 | 6/1999 |
|---|---|---|
| JP | 11-224779 | 8/1999 |
| JP | 2000-327639 | 11/2000 |
| JP | 2001-39933 | 2/2001 |
| JP | 2004-2298 | 1/2004 |
| JP | 2004-83481 | 3/2004 |
| JP | 2004-83483 | 3/2004 |
| JP | 2004-91350 | 3/2004 |
| JP | 2004-107326 | 4/2007 |
| WO | WO 00/39247 | 7/2000 |
| WO | WO 2004/020371 | 3/2004 |
| WO | WO 2004-020372 | 3/2004 |
| WO | WO 2004/020372 | 3/2004 |
| WO | WO 2004/020373 | 3/2004 |
| WO | WO 2004-020373 | 3/2004 |
| WO | WO 2004-020387 | 3/2004 |
| WO | WO 2004/037887 | 5/2004 |
| WO | WO 2006/108497 A1 * | 10/2006 |
| WO | WO 2006/122630 A1 * | 11/2006 |

OTHER PUBLICATIONS

K. Kreger, et al., "Novel Starshaped Molecules Based on Fluorene", Synthetic Metals, 119, 2001, pp. 163-164.

Li Z. H, et al., "Synthesis and Functional Properties of Strongly Luminescent Diphenylamino End-Capped Oligophenylenes", Journal of Organic Chemistry, vol. 69, No. 3, XP002497060, Feb. 6, 2004, 1 Page.

Zhong Hui Li, et al., "Synthesis and Functional Properties of Strongly Luminescent Diphenylamino End-Capped Oligophenylenes", Journal of Organic Chemistry, vol. 69, No. 3, XP002497059, ISSN: 0022-3263, Feb. 6, 2004, pp. 921-927.

Christoph Lambert, et al., "One-and Two-Dimensional Electron Transfer Processes in Triarylamines with Multiple Redox Centers**", Angewandte Chemie International Edition in English, vol. 37, No. 15, XP002497079, 1998, pp. 2107-2110.

* cited by examiner

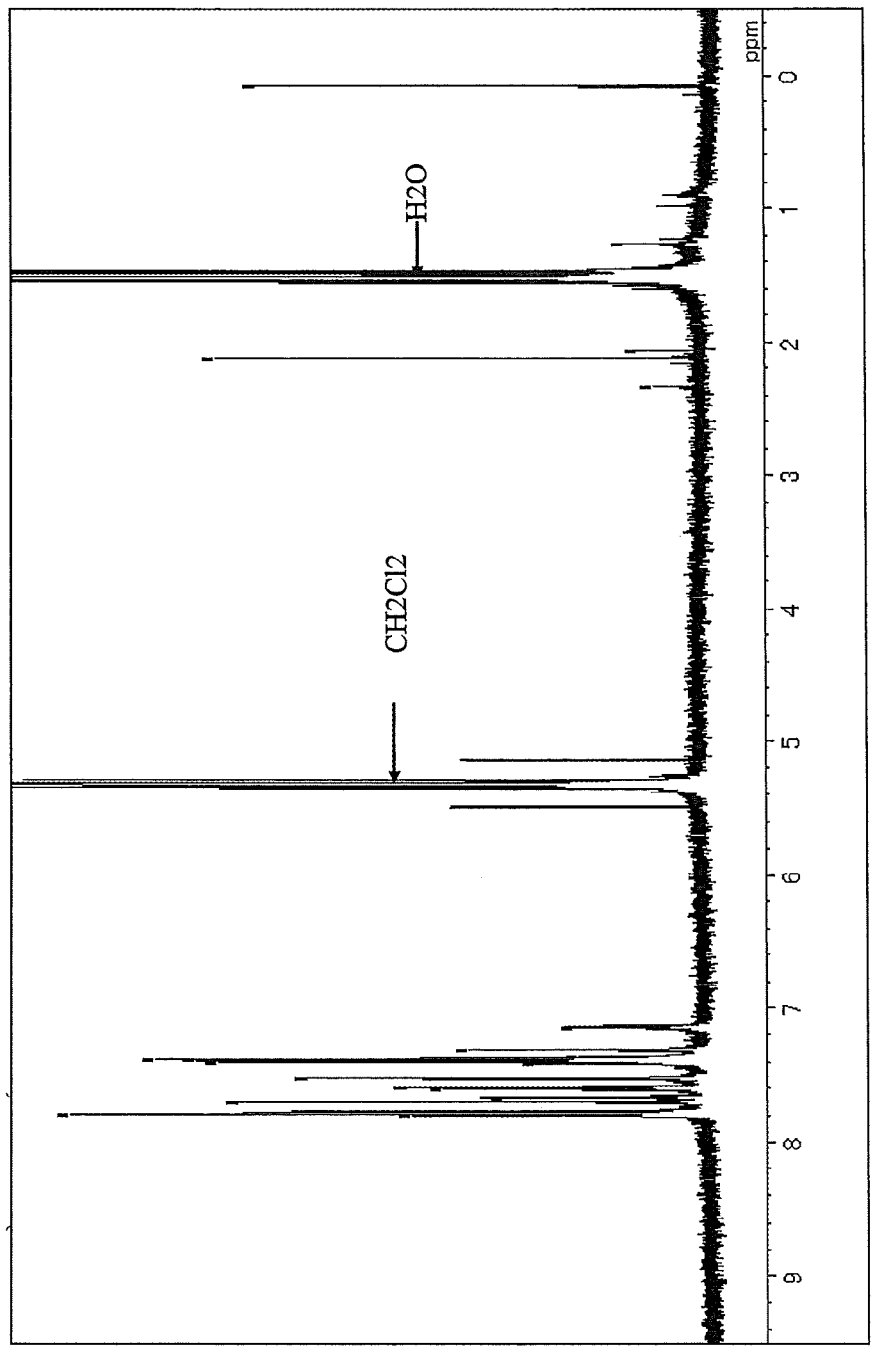

AROMATIC AMINE DERIVATIVE AND ORGANIC ELECTROLUMINESCENCE DEVICE UTILIZING THE SAME

This application is a Continuation of U.S. application Ser. No. 11/909,003, filed on Sep. 18, 2007, which is a National Stage of International Application serial PCT/JP2006/304259, filed on Mar. 6, 2006.

TECHNICAL FIELD

The present invention relates to an aromatic amine derivative and an organic electroluminescent (EL) device using the same. More specifically, the present invention relates to an organic EL device having high emission luminance, high heat resistance, excellent high-temperature storage stability, and a long lifetime and to an aromatic amine derivative for realizing the organic EL device.

BACKGROUND ART

An organic EL device using an organic substance has been used as the flat luminous body of a wall hanging television or as a light source for, for example, the backlight of a display, and has been vigorously developed.

The electroluminescence phenomenon of an organic material was observed in an anthracene single crystal by Pope et al. in 1963 (J. Chem. Phys. 38 (1963) 2042). In 1965, Helfinch and Schneider succeeded in observing relatively strong injection-type EL by means of a solution electrode system having good injection efficiency (Phys. Rev. Lett. 14 (1965) 229). As reported since then, research has been conducted on the formation of an organic light-emitting substance by means of a conjugate organic host substance and a conjugate organic activator having a condensed benzene ring. Examples of the organic host substance include naphthalene, anthracene, phenanthrene, tetracene, pyrene, benzopyrene, chrysene, picene, carbazole, fluorene, biphenyl, terphenyl, triphenylene oxide, dihalobiphenyl, trans-stilbene, and 1,4-diphenylbutadiene Examples of the activator include anthracene, tetracene, and pentacene. However, each of those organic light-emitting substances is present in the form of a single layer having a thickness in excess of 1 µm, so a high electric field is needed to cause such substance to emit light. Therefore, research on a thin film device by means of a vacuum deposition method has been conducted (for example, Thin Solid Films 94 (1982) 171). A reduction in thickness has been effective in reducing a driving voltage, but has not attained a device having luminance high enough to be put into practical use.

In view of the foregoing, Tang et al. have devised an EL device obtained by laminating two extremely thin layers (a hole-transporting layer and a light-emitting layer) between an anode and a cathode by means of a vacuum deposition, and have realized high luminance at a low driving voltage (Non-Patent Document 1 or Patent Document 1). After that, as a result of ten and several years of development of an organic compound to be used in each of the hole-transporting layer and the light-emitting layer, a lifetime and luminous efficiency at practical levels have been achieved. As a result, an organic EL device has started to be practically used in, for example, the display portion of a car stereo or of a cellular phone.

However, the organic EL device has, for example, practically insufficient emission luminous and practically insufficient durability against the deterioration of the device with time due to long-term use, so the additional improvement of the device has been requested. In particular, when one attempts to apply the device to a full-color display or the like, the device is requested to achieve a half life of several thousand hours or longer at a high luminance of 300 cd/m² or more for each of R, G, and B colors. It is difficult to achieve such half life particularly in the case of blue light emission. Blue light emission requires a large energy gap of the light-emitting layer (2.8 eV or more). In addition, an energy barrier upon hole injection between the hole-transporting layer and the light-emitting layer is large. Accordingly, the intensity of an electric field to be applied to an interface between the hole-transporting layer and the light-emitting layer is large. Therefore, the conventional hole-transporting layer has not allowed stable hole injection, so the improvement of the layer has been requested.

In addition, it has been pointed out that the storage performance of the organic EL device at a high temperature equal to or higher than 100° C. is problematic on the precondition that the device is mounted on a vehicle. At this time as well, it has been pointed out that the glass transition temperature of the conventional hole-transporting layer is low. One has attempted to increase the glass transition temperature to 100° C. or higher to cope with the problem. However, this approach has been still insufficient to realize good storage performance at high temperature. Further, there has been a problem in that an exciplex occurs as an interaction between the hole-transporting layer and the light-emitting layer to deteriorate the luminance of the device.

Patent Document 1: U.S. Pat. No. 4,356,429
Non-Patent Document 1: Appl. Phys. Lett. 51 (1987) 913

DISCLOSURE OF THE INVENTION

Problems to be Solved by the Invention

The present invention has been made with a view to solving the above problems, and an object of the present invention is to provide an organic EL device having high emission luminance, high heat resistance, and a long lifetime, and an aromatic amine derivative for realizing the device.

Means for Solving the Problem

The inventors of the present invention have made extensive studies with a view to achieving the above object. As a result, the inventors have found that the use of a novel aromatic amine derivative represented by the following general formula (1) as a material for an organic EL device can improve the emission luminance, heat resistance, and lifetime of an organic EL device to be obtained. Thus, the inventors have completed the present invention.

That is, the present invention provides an aromatic amine derivative represented by any one of the following general formulae (1) to (4):

[Formula 1]

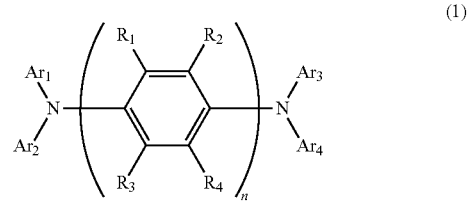

(1)

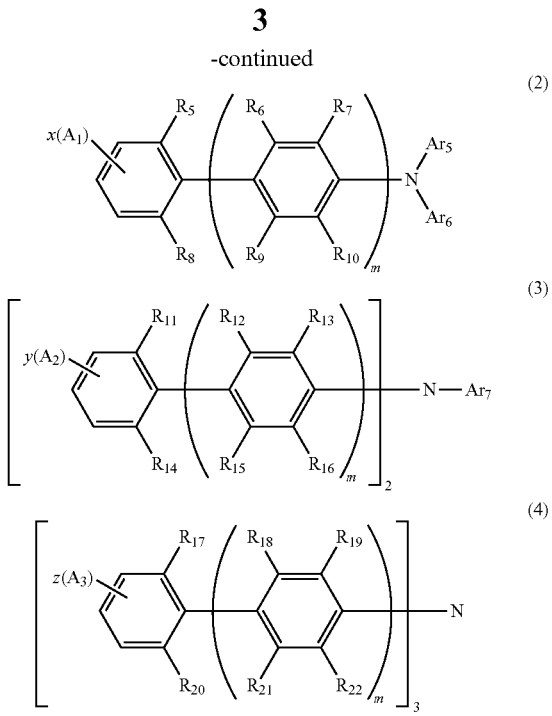

in the general formulae (1) to (4):

Ar₁ to Ar₇ each independently represent a substituted or unsubstituted aryl group having 5 to 40 ring carbon atoms, or a substituted or unsubstituted heterocyclic group having 5 to 40 ring atoms, and may be identical to or different from one another, provided that a case where a substituent in each of the groups represented by $Ar_1$, $Ar_2$, $Ar_3$, and $Ar_4$ comprises a group containing a vinyl group is excluded;

$R_1$ to $R_{22}$ and $A_1$ to $A_3$ each independently represent a hydrogen atom, a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group substituted by a substituted or unsubstituted aryl group having 5 to 50 ring carbon atoms, a substituted or unsubstituted silyl group, a halogen atom, a cyano group, a nitro group, a hydroxyl group, or a carboxyl group;

n represents an integer of 3 to 6, and m represents an integer of 2 to 5; and x, y, and z each represent an integer of 0 to 3, and, when x, y, or z represents 2 or more, $A_1$'s, $A_2$'s, or $A_3$'s may be identical to or different from each other, and in the general formula (1), in at least one of combinations of "$R_1$ and $R_2$" and "$R_3$ and $R_4$", "$R_1$ and $R_2$" or "$R_3$ and $R_4$" are bonded to each other to form a substituted or unsubstituted ring, in the general formula (2), in at least one of combinations of "$R_5$ and $R_6$" "$R_6$ and $R_7$", "$R_8$ and $R_9$", and "$R_9$ and $R_{10}$", "$R_5$ and $R_6$", "$R_6$ and $R_7$", "$R_8$ and $R_9$", or "$R_9$ and $R_{10}$" are bonded to each other to form a substituted or unsubstituted ring, in the general formula (3), in at least one of combinations of "$R_{11}$ and $R_{12}$", "$R_{12}$ and $R_{13}$", "$R_{14}$ and $R_{15}$", and "$R_{15}$ and $R_{16}$", "$R_{11}$ and $R_{12}$", "$R_{12}$ and $R_{13}$" "$R_{14}$ and $R_{15}$", or "$R_{15}$ and $R_{16}$" are bonded to each other to form a substituted or unsubstituted ring, and in the general formula (4), in at least one of combinations of "$R_{17}$ and $R_{18}$", "$R_{18}$ and $R_{19}$", "$R_{20}$ and $R_{21}$", and "$R_{21}$ and $R_{22}$", "$R_{17}$ and $R_{18}$", "$R_{18}$ and $R_{19}$", "$R_{20}$ and $R_{21}$", or "$R_{21}$ and $R_{22}$" are bonded to each other to form a substituted or unsubstituted ring.

In addition, the present invention provides also an organic EL device including an organic thin film layer composed of one or more layers including at least a light emitting layer, the organic thin film layer being interposed between a cathode and an anode, in which at least one layer of the organic thin film layer contains the aromatic amine derivative alone or as a component of a mixture.

Effect of the Invention

Each of the aromatic amine derivative of the present invention and the organic EL device using the derivative has high emission luminance, high heat resistance, excellent high-temperature storage stability, and a long lifetime.

BRIEF DESCRIPTION OF THE DRAWINGS

The FIGURE depicts a view showing the ¹H-NMR spectrum of Compound (5) obtained in Synthesis Example 3.

BEST MODES FOR CARRYING OUT THE INVENTION

An aromatic amine derivative of the present invention is represented by any one of the following general formulae (1) to (4):

[Formula 2]

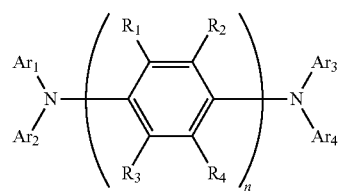

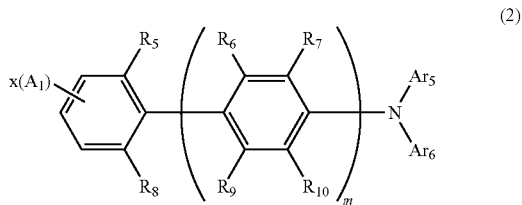

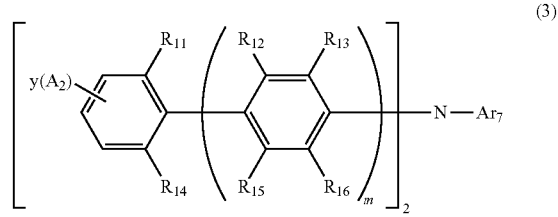

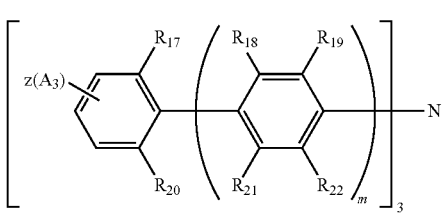

(4)

where:

Ar$_1$ to Ar$_7$ each independently represent a substituted or unsubstituted aryl group having 5 to 40 ring carbon atoms, or a substituted or unsubstituted heterocyclic group having 5 to 40 ring atoms, and may be identical to or different from one another, provided that a case where a substituent in each of the groups represented by Ar$_1$, Ar$_2$, Ar$_3$, and Ar$_4$ includes a group containing a vinyl group is excluded.

In addition, the substituted or unsubstituted aryl group having 5 to 40 ring carbon atoms represented by any one of Ar$_1$ to Ar$_7$ is preferably an aryl group having 5 to 40 ring carbon atoms which is substituted by an aryl group, an alkyl group, an alkoxy group, an aralkyl group, an aryloxy group, an arylthio group, or an alkoxycarbonyl group, or is unsubstituted, and specific examples of those groups include those described later for R$_1$ to R$_{22}$ and A$_1$ to A$_3$.

Examples of aryl groups of Ar$_1$ to Ar$_7$ and heterocyclic ring groups include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, a fluoranthenyl group, a fluorenyl group, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Of those, a phenyl group, a naphthyl group, a biphenyl group, an anthranyl group, a phenanthryl group, a pyridinyl group, a pyrenyl group, a chrysenyl group, a fluoranthenyl group, and a fluorenyl group are preferable.

In the general formulae (1) to (4), R$_1$ to R$_{22}$ and A$_1$ to A$_3$ each independently represent a hydrogen atom, a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group substituted with a substituted or unsubstituted aryl group having 5 to 50 carbon atoms, a substituted or unsubstituted silyl group, a halogen atom, a cyano group, a nitro group, a hydroxyl group, and a carboxyl group.

Examples of a substituted or unsubstituted aryl group having 5 to 50 ring carbon atoms in any one of the $R_1$ to $R_{22}$ and $A_1$ to $A_3$ include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group, a fluoroanthenyl group, a fluorenyl group, a 1-pyrrolyl group, a 2-pyrrolyl group, a 3-pyrrolyl group, a pyradinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenadinyl group, a 2-phenadinyl group, a 1-phenothiadinyl group, a 2-phenothiadinyl group, a 3-phenothiadinyl group, a 4-phenothiadinyl group, a 10-phenothiadinyl group, a 1-phenoxadinyl group, a 2-phenoxadinyl group, a 3-phenoxadinyl group, a 4-phenoxadinyl group, a 10-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Of those, a phenyl group, a naphthyl group, a biphenyl group, an anthranyl group, a phenanthryl group, a pyrenyl group, a chrysenyl group, a fluoranthenyl group, or a fluorenyl group is preferable.

Examples of the substituted or unsubstituted alkyl group having 1 to 50 carbon atoms in any one of the $R_1$ to $R_{22}$ and $A_1$ to $A_3$ include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms in any one of the $R_1$ to $R_{22}$ and $A_1$ to $A_3$ is represented by —OY, and examples of Y include the same examples as those described for the above-mentioned alkyl group.

Examples of the substituted or unsubstituted aralkyl group having 6 to 50 ring carbon atoms in any one of the $R_1$ to $R_{22}$ and $A_1$ to $A_3$ include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

The substituted or unsubstituted aryloxy group having 5 to 50 ring carbon atoms for each of the $R_1$ to $R_{22}$ and $A_1$ to $A_3$ is represented by —OY', and examples of Y' include examples similar to those described for the aryl group represented by any one of $Ar_2$ to $Ar_4$.

The substituted or unsubstituted arylthio group having 5 to 50 ring carbon atoms for each of the $R_1$ to $R_{22}$ and $A_1$ to $A_3$ is represented by —SY', and examples of Y' include examples similar to those described for the aryl group represented by any one of $Ar_2$ to $Ar_4$.

The substituted or unsubstituted alkoxycarbonyl group having 1 to 50 carbon atoms for each of the $R_1$ to $R_{22}$ and $A_1$ to $A_3$ is a group represented by —COOY, and examples of Y include examples similar to those described for the alkyl group.

Examples of a substituted or unsubstituted aryl group having 5 to 50 ring carbon atoms in the amino group substituted by the aryl group for each of the $R_1$ to $R_{22}$ and $A_1$ to $A_3$ include examples similar to those described for the aryl group represented by any one of $Ar_1$ to $Ar_7$.

Examples of the silyl group represented by any one of $R_1$ to $R_{22}$ and $A_1$ to $A_3$ include a trimethylsilyl group, a triethylsilyl group, a t-butyldimethylsilyl group, a vinyldimethylsilyl group, and a propyldimethylsilyl group.

Examples of the halogen atom as a substituent for each of the $R_1$ to $R_{22}$ and $A_1$ to $A_3$ include a fluorine atom, a chlorine atom, a bromine atom, and an iodine atom.

In addition, examples of substituents for the respective groups in the general formulae (1) to (4) include: an alkyl group having 1 to 10 carbon atoms (such as a methyl group, an ethyl group, an i-propyl group, an n-propyl group, an n-butyl group, an s-butyl group, a t-butyl group, an n-pentyl group, a cyclopentyl group, an n-hexyl group, or a cyclohexyl group); an alkoxy group having 1 to 10 carbon atoms (such as an ethoxy group, a methoxy group, an i-propoxy group, an n-propoxy group, an s-butoxy group, a t-butoxy group, a pentoxy group, a hexyloxy group, a cyclopentoxy group, or a cyclohexyloxy group); an aryl group having 5 to 40 ring carbon atoms; an amino group substituted by an aryl group having 5 to 40 ring carbon atoms; a cyano group; a nitro group; and a halogen atom. Of those, an alkyl group having 1 to 10 carbon atoms, and an alkoxy group having 1 to 10 carbon atoms are preferable, an alkyl group having 1 to 6 carbon atoms is more preferable, and a methyl group, an ethyl group, an i-propyl group, an n-propyl group, an n-butyl group, an s-butyl group, a t-butyl group, an n-pentyl group, a cyclopentyl group, an n-hexyl group, or a cyclohexyl group is particularly preferable.

In the general formula (1), n represents an integer of 3 to 6, or preferably 3 to 5.

In each of the general formulae (2) to (4), m represents an integer of 2 to 5, or preferably 2 to 4.

In the general formulae (2) to (4), x, y, and z each represent an integer of 0 to 3, and, when x, y, or z represents 2 or more, $A_1$'s, $A_2$'S, or $A_3$'s may be identical to or different from each other.

In the general formula (1), in at least one of combinations of "$R_1$ and $R_2$" and "$R_3$ and $R_4$", "$R_1$ and $R_2$" or "$R_3$ and $R_4$" are bonded to each other to form a substituted or unsubstituted ring. In the general formula (2), in at least one of combinations of "$R_5$ and $R_6$", "$R_6$ and $R_7$", "$R_8$ and $R_9$", and "$R_9$ and $R_{10}$", "$R_5$ and $R_6$", "$R_6$ and $R_7$", "$R_8$ and $R_9$" or "$R_9$ and $R_{10}$" are bonded to each other to form a substituted or unsubstituted ring. In the general formula (3), in at least one of combinations of "$R_{11}$ and $R_{12}$" "$R_{12}$ and $R_{13}$", "$R_{14}$ and $R_{15}$", and "$R_{15}$ and $R_{16}$", "$R_{11}$ and $R_{12}$", "$R_{12}$ and $R_{13}$", "$R_{14}$ and $R_{15}$", or "$R_{15}$ and $R_{16}$" are bonded to each other to form a substituted or unsubstituted ring. In the general formula (4), in at least one of combinations of "$R_{17}$ and $R_{18}$", "$R_{18}$ and $R_{19}$", "$R_{20}$ and $R_{21}$", and "$R_{21}$ and $R_{22}$", "$R_{17}$ and $R_{18}$", "$R_{18}$ and $R_{19}$", "$R_{20}$ and $R_{21}$", or "$R_{21}$ and $R_{22}$" are bonded to each other to form a substituted or unsubstituted ring.

Examples of such ring include: cycloalkanes each having 4 to 12 ring carbon atoms such as cyclobutane, cyclopentane, cyclohexane, adamantane, and norbornane; cycloalkenes each having 4 to 12 ring carbon atoms such as cyclobutene, cyclopentene, cyclohexene, cycloheptene, and cyclooctene; cycloalkadienes each having 5 to 12 ring carbon atoms such as cyclopentadiene, cyclohexadiene, cycloheptadiene, and cyclooctadiene; aromatic rings each having 6 to 50 ring carbon atoms such as benzene, naphthalene, phenanthrene, anthracene, pyrene, chrysene, and acenaphthylene; and heterocyclic rings each having 5 to 50 ring atoms such as imidazole, pyrrole, furan, thiophene, and pyridine. Of those, five-membered rings and six-membered rings are preferable, and five-membered rings are particularly preferable. In addition, examples of a substituent for such ring include examples similar to those described above.

In the general formula (1), in at least one of combinations of "$R_1$ and $R_2$", "$R_1$ and $R_2$" are particularly preferably bonded to each other to form a substituted or unsubstituted, five- or six-membered ring. In the general formula (2), in at least one of combinations of "$R_5$ and $R_6$" and/or "$R_6$ and $R_7$", "$R_5$ and $R_6$" and/or "$R_6$ and $R_7$" are particularly preferably bonded to each other to form a substituted or unsubstituted, five- or six-membered ring. In the general formula (3), in at least one of combinations of "$R_{11}$ and $R_{12}$" and/or "$R_{12}$ and $R_{13}$", "$R_{11}$ and $R_{12}$" and/or "$R_{12}$ and $R_{13}$" are particularly preferably bonded to each other to form a substituted or unsubstituted, five- or six-membered ring. In the general formula (4), in at least one of combinations of "$R_{17}$ and $R_{18}$" and/or "$R_{18}$ and $R_{19}$", "$R_{17}$ and $R_{18}$" and/or "$R_{18}$ and $R_{19}$" are particularly preferably bonded to each other to form a substituted or unsubstituted, five- or six-membered ring.

The aromatic amine derivative represented by the general formula (1) of the present invention is preferably an aromatic amine derivative represented by the following general formula (1-a), (1-b), or (1-c):

[Formula 3]

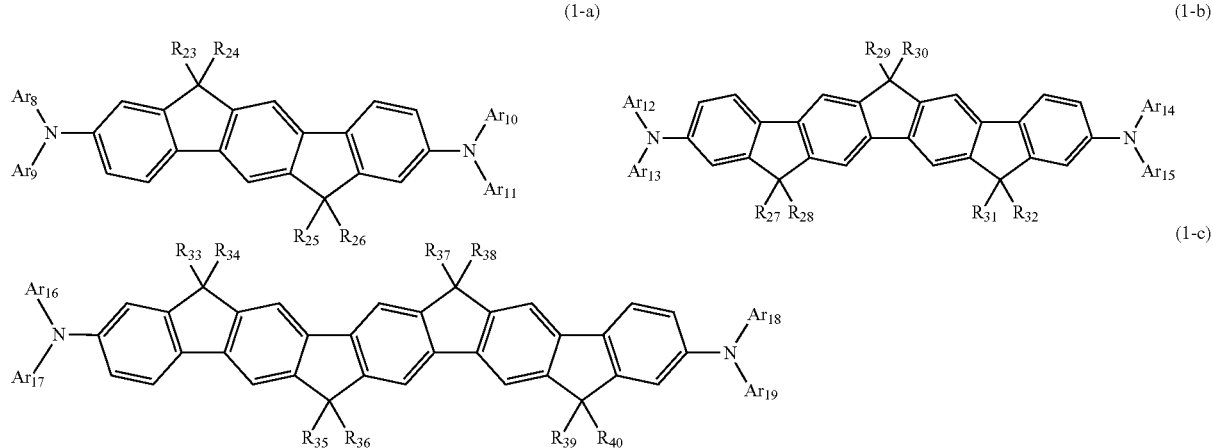

(1-a) (1-b) (1-c)

where $Ar_8$ to $Ar_{19}$ each have the same meaning as that of any one of $Ar_1$ to $Ar_4$ described above, $R_{23}$ to $R_{40}$ each have the same meaning as that of any one of $R_1$ to $R_4$ described above, and specific examples and preferable examples of each of these groups include examples similar to those described above, provided that the case where a substituent in each of the groups represented by $Ar_8$ to $Ar_{19}$ is a group containing a vinyl group is excluded.

The aromatic amine derivative represented by the general formula (2) of the present invention is preferably an aromatic amine derivative represented by the following general formula (2-a), (2-b), or (2-c):

[Formula 4]

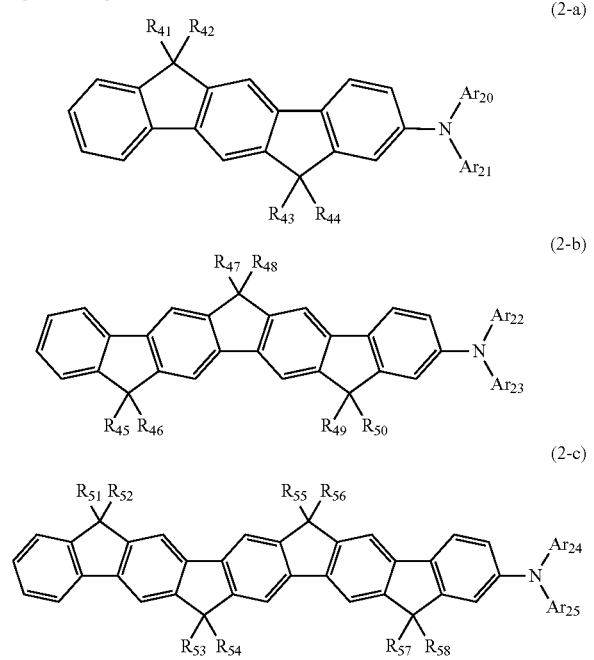

(2-a) (2-b) (2-c)

where $Ar_{20}$ to $Ar_{25}$ each have the same meaning as that of any one of $Ar_5$ to $Ar_6$ described above, $R_{41}$ to $R_{58}$ each have the same meaning as that of any one of $R_5$ to $R_{10}$ described above, and specific examples and preferable examples of each of these groups include examples similar to those described above.

The aromatic amine derivative represented by the general formula (3) of the present invention is preferably an aromatic amine derivative represented by the following general formula (3-a) or (3-b):

[Formula 5]

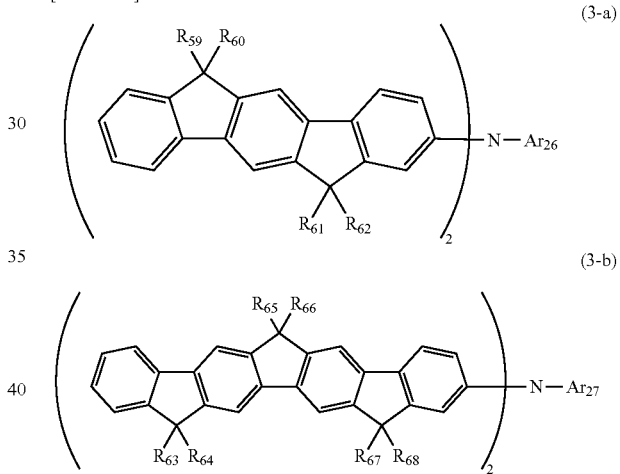

(3-a) (3-b)

where $Ar_{26}$ to $Ar_{27}$ each have the same meaning as that of $Ar_7$ described above, $R_{59}$ to $R_{68}$ each have the same meaning as that of any one of $R_{11}$ to $R_{16}$ described above, and specific examples and preferable examples of each of these groups include examples similar to those described above.

The aromatic amine derivative represented by the general formula (4) of the present invention is preferably an aromatic amine derivative represented by the following general formula (4-a) or (4-b):

[Formula 6]

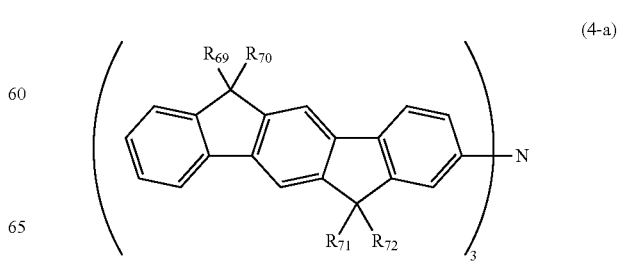

(4-a)

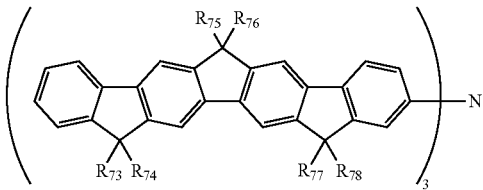

(4-b)

where $R_{69}$ to $R_{78}$ each have the same meaning as that of any one of $R_{17}$ to $R_{22}$ described above, and specific examples and preferable examples of each of these groups include examples similar to those described above.

The aromatic amine derivative of the present invention is preferably a material for an organic EL device, or is more preferably a hole-transporting material for an organic EL device or a doping material for an organic EL device.

Specific examples of the aromatic amine derivative represented by each of the general formulae (1) to (4) of the present invention are shown below. However, the aromatic amine derivative is not limited to these exemplified compounds.

[Formula 7]

(1)

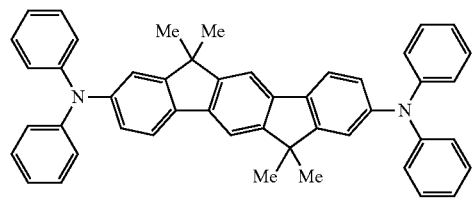

(2)

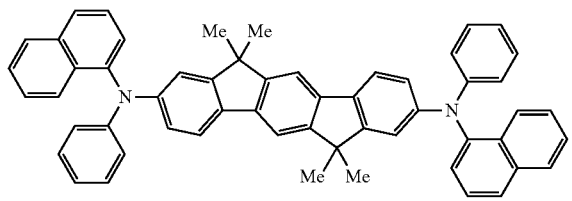

(3)

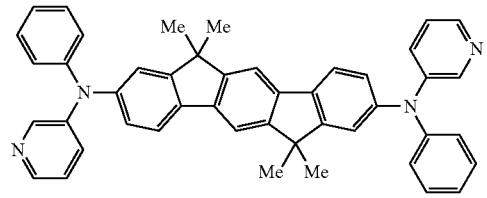

(4)

(5)

(6)

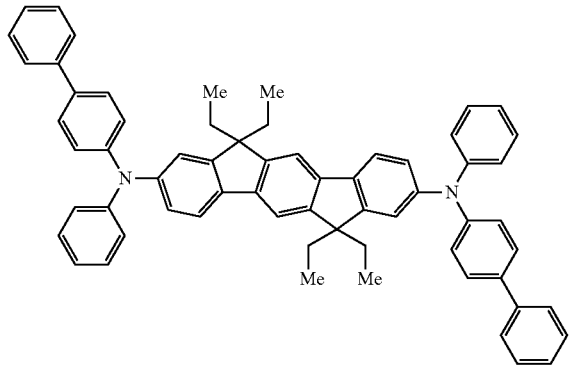

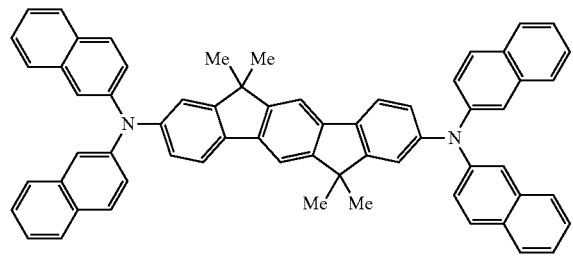

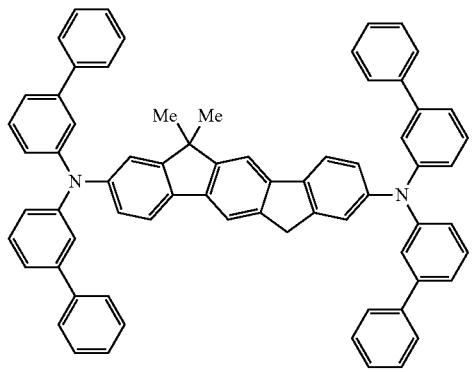

-continued
(7)
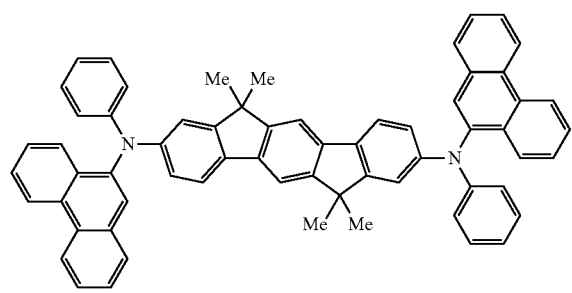
(8)
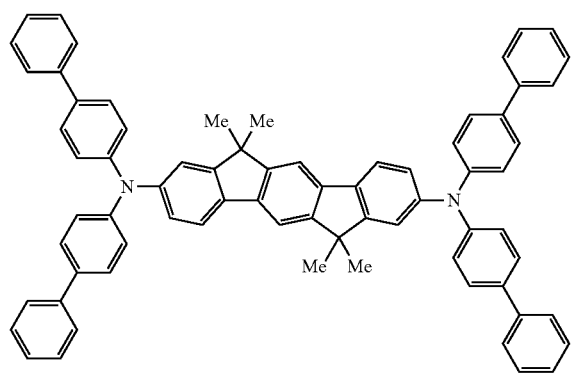
(9)
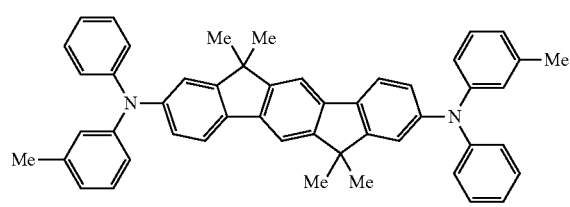
[Formula 8]
(10)
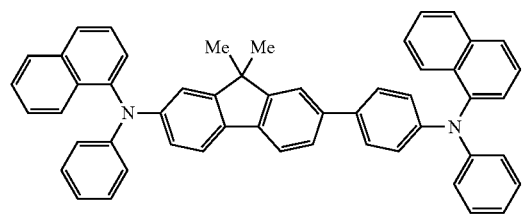
(11)
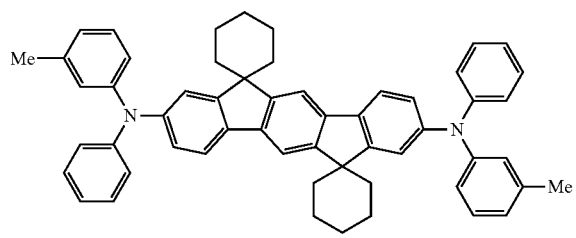
(12)
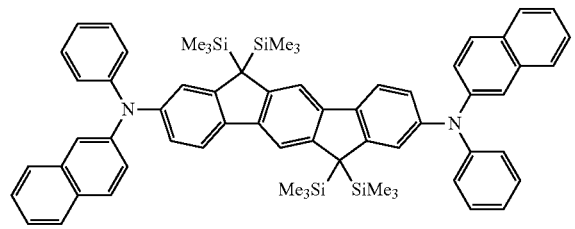
(13)
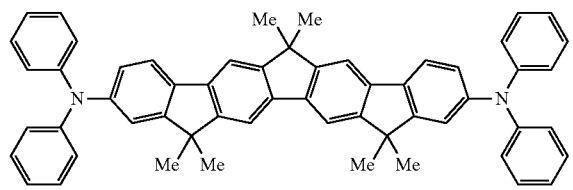
(14)
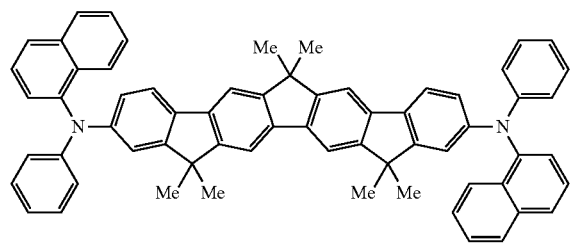
(15)
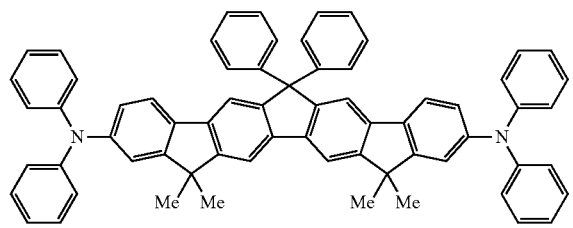

-continued
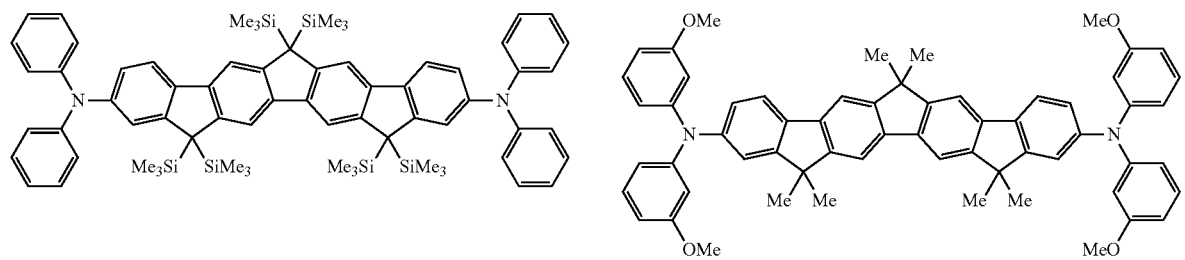
(16)
(17)
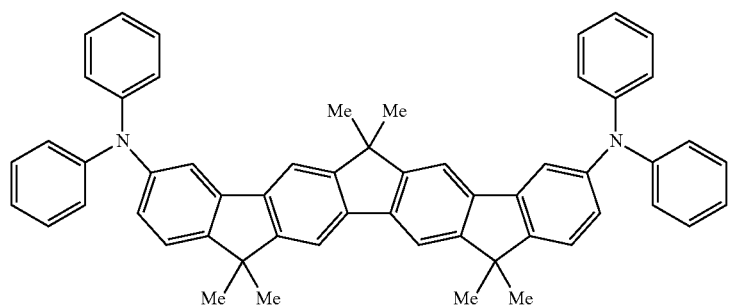
(18)
[Formula 9]
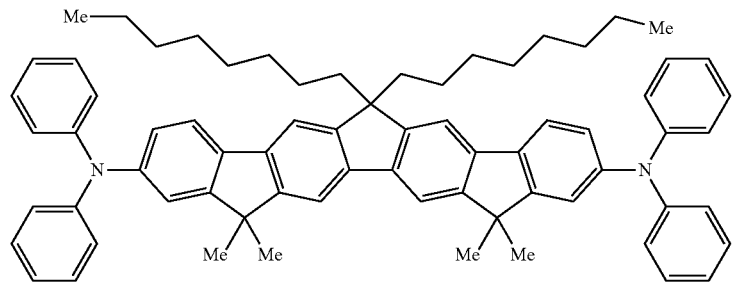
(19)
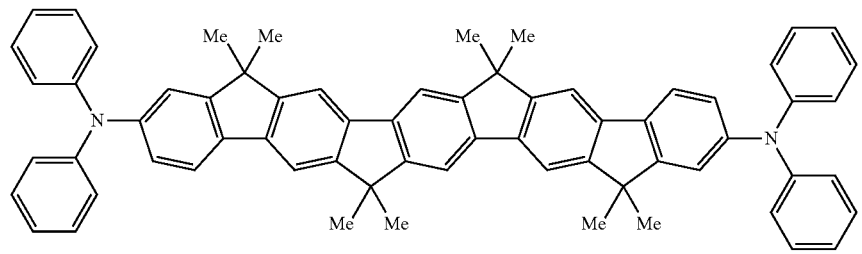
(20)
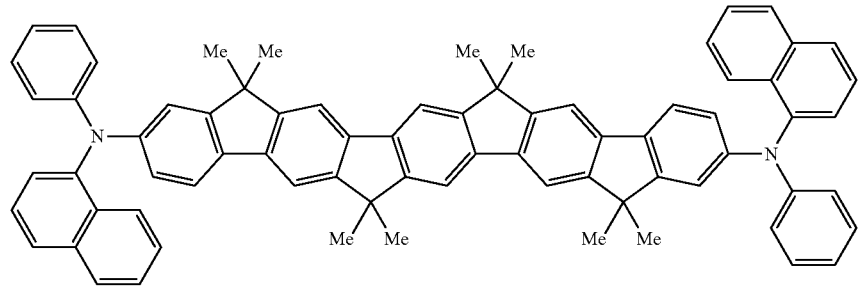
(21)

(22)
(23)
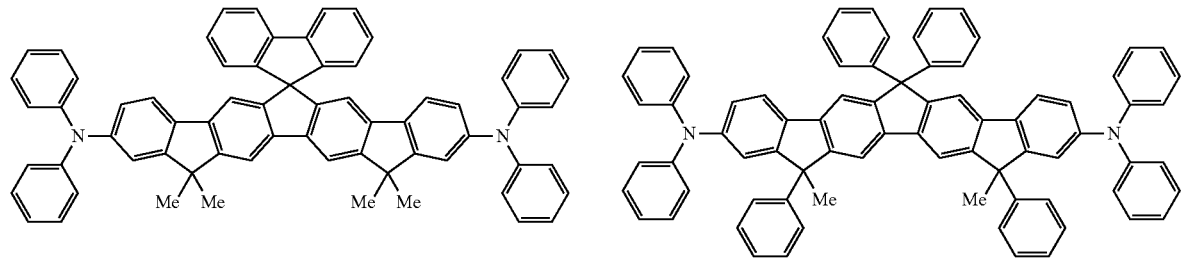
(24)
(25)
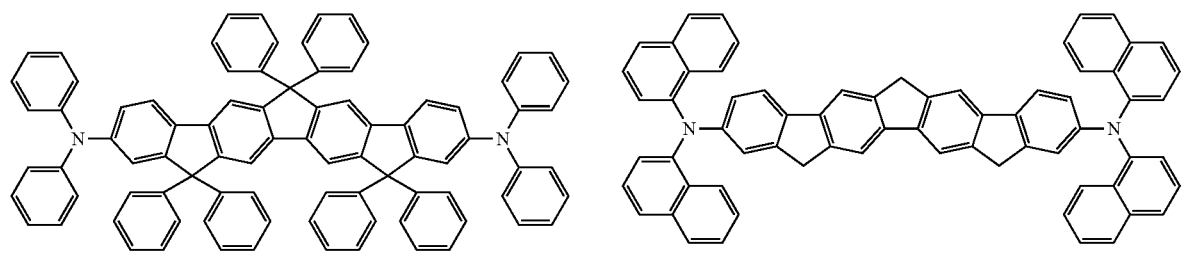
(26)
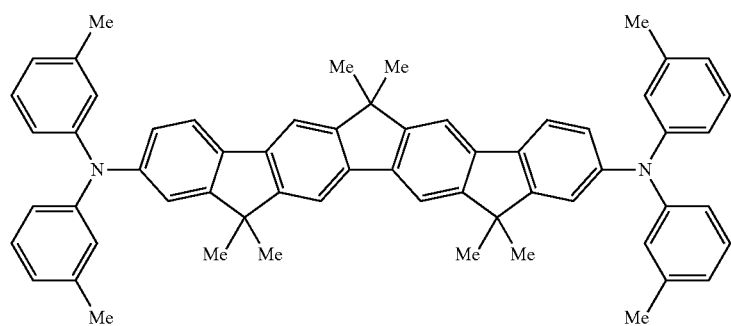
(27)
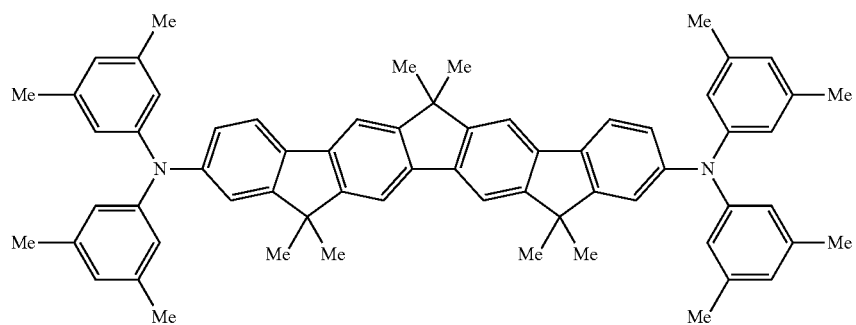
[Formula 10]
(28)
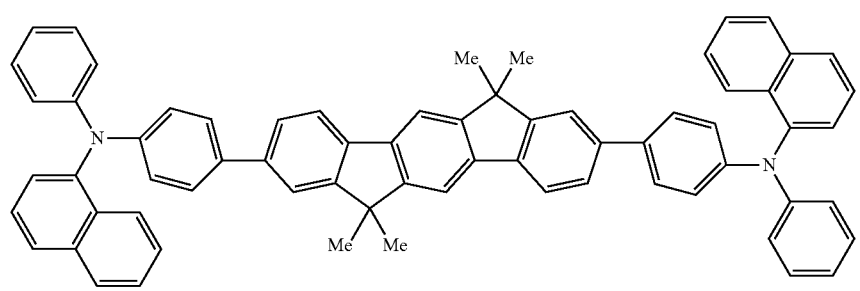

(29)
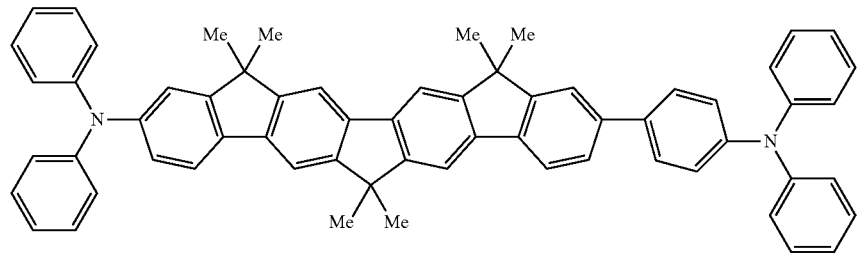
(30)
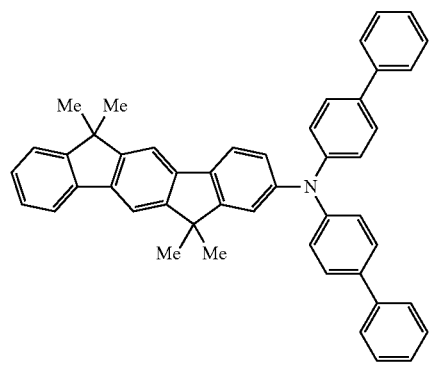
(31)
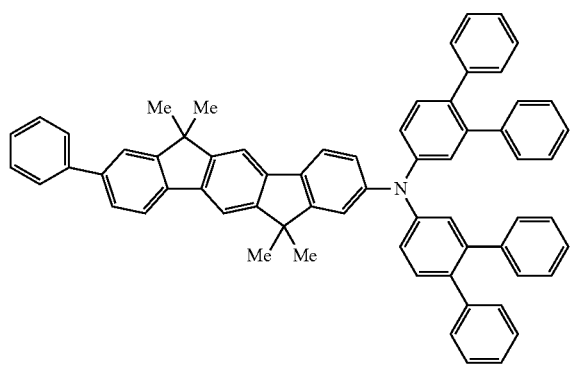
(32)
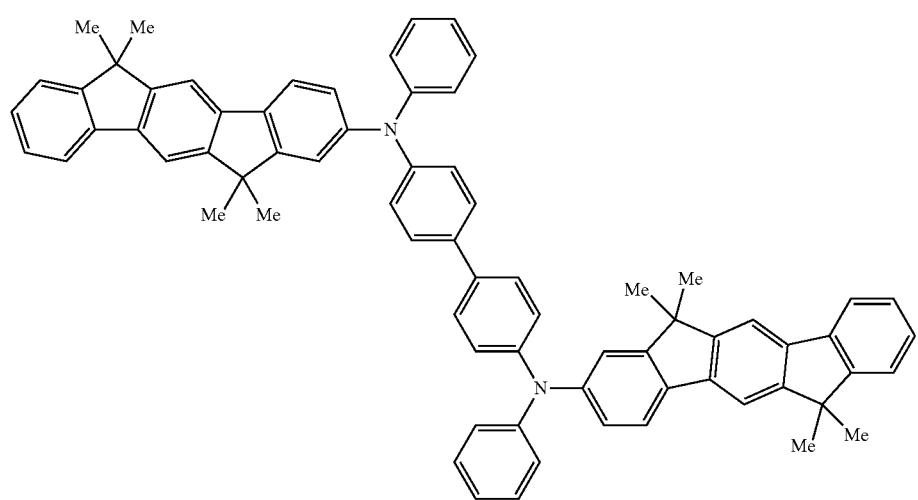

-continued
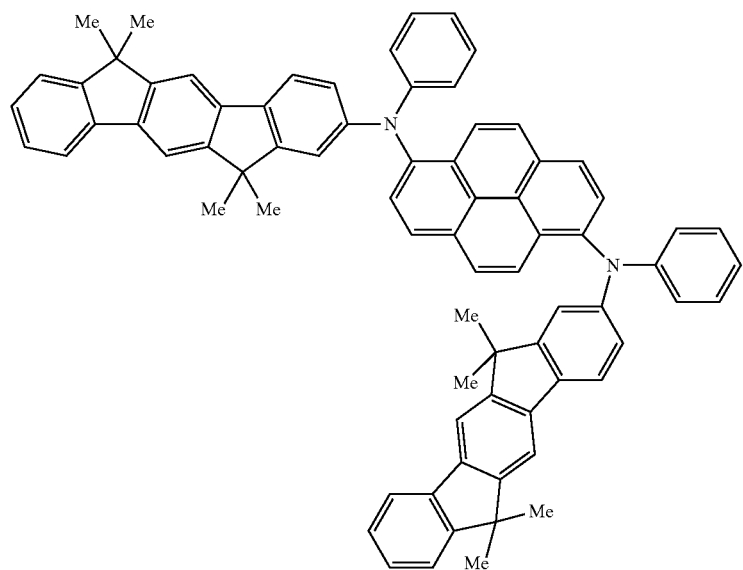
(33)
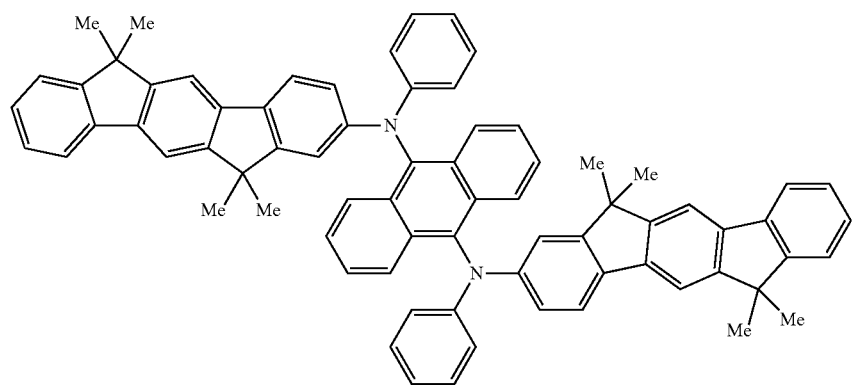
(34)
[Formula 11]
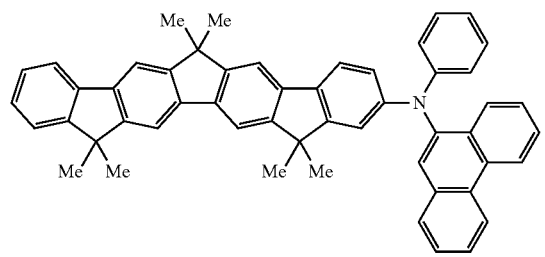
(35)
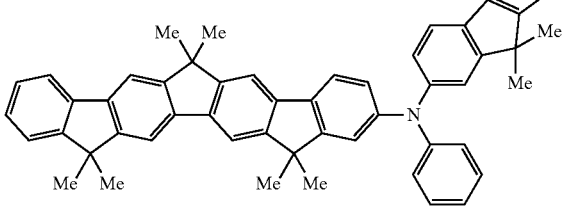
(36)
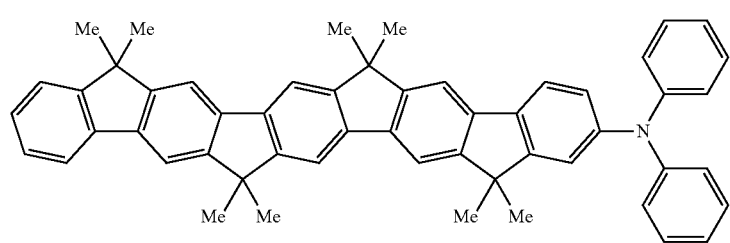
(37)

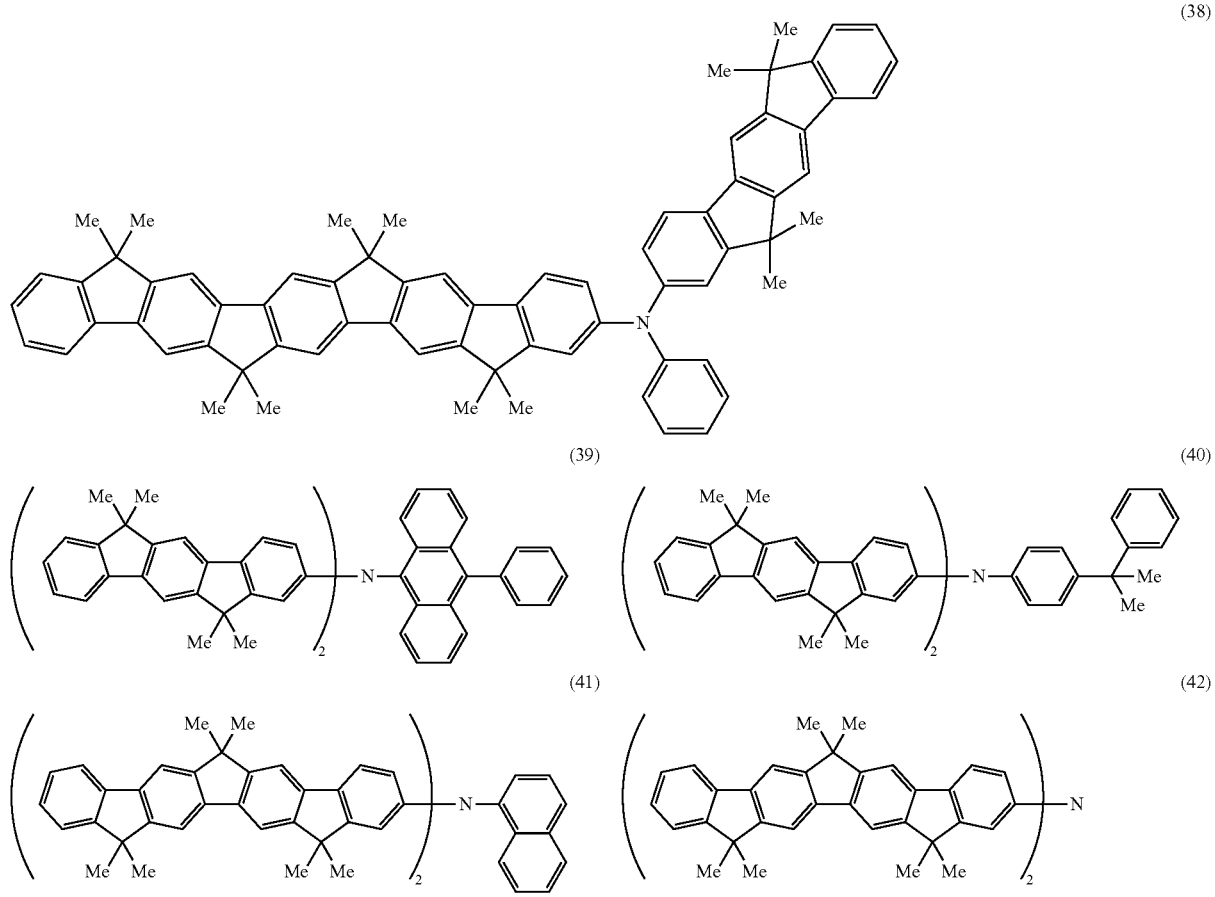

Next, a method of producing the aromatic amine derivative of the present invention will be described.

A method of producing the aromatic amine derivative represented by the general formula (1) of the present invention is not particularly limited, and it is sufficient to produce the derivative by a known method. A condensed oligofluorene compound is derived by, for example, a method reported in "the 84th spring annual meeting of the Chemical Society of Japan 3E1-33 (2004) (Makoto Kimura et al.)" or "a method described in J. Am. Chem. Soc., 126, 6987-6995 (2004) (Josemon Jacob et al.)".

Subsequently, the condensed oligofluorene compound is halogenated, whereby a halogen derivative of a condensed oligofluorene is synthesized. Examples of a reagent for use in the halogenation when a halogen atom for use in the halogenation is bromine include bromine, N-bromosuccinimide (NBS), KBr, $KBrO_3$, $AlBr_3$, $PBr_3$, $SbBr_3$, $FeBr_2$, $PyHBrCl_2$, and $Bu_4NBr_3$. Of those, bromine and NBS are preferable. Examples of a reagent for use in the halogenation when a halogen atom for use in the halogenation is a halogen atom except bromine include products each obtained by replacing bromine in each of those examples with the corresponding halogen atom.

In addition, the halogenation is preferably performed in an organic solvent such as carbon tetrachloride, chloroform, methylene chloride, acetic acid, pyridine, or dimethylformamide (DMF), or in sulfuric acid. In addition, a reaction system may be added with a peroxide such as benzoyl peroxide (BPO), 2,2'-azobisisobutyronitrile (AIBN), or m-chloroperbenzoic acid (mCPBA), or a heavy metal salt, or may be irradiated with light.

A reaction temperature at the time of the halogenation ranges from typically room temperature to 150° C., or preferably room temperature to 100° C., and a reaction time at the time of the halogenation ranges from typically 1 to 120 hours, or preferably 6 to 18 hours.

Next, the halogen derivative is aminated with a diarylamine, whereby an aromatic amine is produced. A transition metal is preferably used as a catalyst at the time of the amination.

Examples of the transition metal include manganese (Mn), iron (Fe), cobalt (Co), nickel (Ni), copper (Cu), palladium (Pd), molybdenum (Mo), rhodium (Rh), ruthenium (Ru), vanadium (V), chromium (Cr), platinum (Pt), and iridium (Ir). Of those, Ni, Pd, Pt, and Cu are preferable, and Pd and Cu are more preferable.

An elementary substance of each of those transition metals is preferably used in the form of, for example, a fine powder. In addition, each of the metals is preferably used in the form of, for example, a transition metal complex or a transition metal compound.

Next, the organic EL device of the present invention will be described.

The organic EL device of the present invention includes one or multiple organic thin film layers including at least a light-emitting layer, the one or multiple organic thin film layers being interposed between the cathode and the anode, in which at least one layer of the one or multiple organic thin film layers contains the aromatic amine derivative of the present invention alone or as a component of a mixture.

It is preferable that, in the organic EL device of the present invention, the one or multiple organic thin film layers have a hole-transporting layer, and the hole-transporting layer contains the aromatic amine derivative of the present invention alone or as a component of a mixture. Further, it is preferable that the main component of the hole-transporting layer be the aromatic amine derivative of the present invention.

Further, it is more preferable that, in the organic EL device of the present invention, the light-emitting layer contain the aromatic amine derivative of the present invention alone or as a component of a mixture. It is still more preferable that the light-emitting layer contain the aromatic amine derivative of the present invention as a doping material.

The aromatic amine derivative of the present invention is particularly preferable as an organic EL device emitting blue-based light.

In the present invention, the organic EL device having multiple organic thin film layers is a laminate having, for example, an (anode/hole-injecting layer/light-emitting layer/cathode), (anode/light-emitting layer/electron-injecting layer/cathode), or (anode/hole-injecting layer/light-emitting layer/electron-injecting layer/cathode) constitution.

In addition to the aromatic amine derivative of the present invention, an additional known light-emitting material, doping material, hole-injecting material, or electron-injecting material can be used as required in the multiple layers. When the organic EL device has the multiple organic thin film layers, a reduction in luminance or lifetime due to quenching can be prevented. If needed, a light-emitting material, a doping material, a hole-injecting material, and an electron-injecting material can be used in combination. In addition, a doping material can provide improvements in emission luminance and luminous efficiency, and red or blue light emission. In addition, each of the hole-injecting layer, the light-emitting layer, and the electron-injecting layer may be formed of a layer constitution having two or more layers. At that time, in the case of the hole-injecting layer, a layer for injecting a hole from the electrode is referred to as a hole-injecting layer, and a layer for receiving the hole from the hole-injecting layer and transporting the hole to the light-emitting layer is referred to as a hole-transporting layer. In the same manner, in the case of the electron-injecting layer, a layer for injecting an electron from the electrode is referred to as an electron-injecting layer, and a layer for receiving the electron from the electron-injecting layer and transporting the electron to the light-emitting layer is referred to as an electron-transporting layer. Each of those layers is selected and used depending on factors such as the energy level of a material, heat resistance, and adhesiveness between the layer and an organic layer or a metal electrode.

Examples of a host material or a doping material available for the light-emitting layer together with the aromatic amine derivative of the present invention include, but not limited to: for example, large amounts of condensed aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethynylanthracenyl)benzene and derivatives thereof; organic metal complexes such as tris(8-quinolinolato)aluminum or bis-(2-methyl-8-quinolinolato)-4-(phenylphenolinato)aluminum; a triarylamine derivative, a styrylamine derivative, a stilbene derivative, a coumarin derivative, a pyrane derivative, an oxazone derivative, a benzothiazole derivative, a benzoxazole derivative, a benzoimidazole derivative, a pyrazine derivative, a cinnamate derivative, a diketopyrrolopyrrole derivative, an acridone derivative, and quinacridone derivative.

A compound having an ability of transporting a hole, having hole injection efficiency from an anode and excellent hole injection efficiency to a light-emitting layer or a light-emitting material, preventing the migration of an exciton generated in the light-emitting layer to an electron-injecting layer or an electron-injecting material, and having excellent thin film-formability is preferable as a hole-injecting material. Specific examples of the compound include, but not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Out of available hole-injecting materials in the organic EL device of the present invention, additional effective hole-injecting materials are an aromatic tertiary amine derivative and a phthalocyanine derivative.

An example of the aromatic tertiary amine derivative includes, but not limited to, for example, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, or N,N-bis(4-di-4-tolylaminophenyl)-4-phenyl-cyclohexane, or an oligomer or a polymer having those aromatic tertiary amine skeletons.

Examples of the phthalocyanine (Pc) derivative include, but not limited to, for example, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc, and naphthalocyanine derivatives.

In addition, the organic EL device of the present invention is preferably formed of a layer containing each of those aromatic tertiary amine derivatives and/or each of phthalocyanine derivatives between a light-emitting layer and an anode, for example, the hole-transporting layer or the hole-injecting layer.

A compound having an ability of transporting electrons, having electron injection efficiency from a cathode and excellent electron injection efficiency to a light-emitting layer or a light-emitting material, preventing the migration of an exciton generated in the light-emitting layer to the hole-injecting layer, and having excellent thin film-formability is preferable as an electron-injecting material. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. In addition, an electron-accepting substance can be added to the hole-injecting material or an electron-donating substance can be added to the electron-injecting material to thereby intensify the hole-injecting material or the electron-injecting material, respectively.

In the organic EL device of the present invention, additional effective electron-injecting materials are a metal complex compound and a nitrogen-containing five-membered ring derivative.

Examples of the metal complex compound include, but not limited to, for example, 8-hydroxyquinolinato lithium, bis(8-hydroxyquinolinato)zinc, bis(8-hydroxyquinolinato) copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis (10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the preferred nitrogen-containing five-membered derivative include, for example, an oxazole derivative, a thiazole derivative, an oxadiazole derivative, a thiadiazole derivative, and a triazole derivative. Specific examples of the derivative include, but not limited to, 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4''-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to the aromatic amine derivative, at least one kind of a light-emitting material, a doping material, a hole-injecting material, and an electron-injecting material may be incorporated into any one of the organic thin film layers. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device of the present invention. Examples of an available conductive material include: carbon, aluminum, vanadium, iron, cobalt, nickel, tungsten, silver, gold, platinum, and palladium, and alloys of them; metal oxides such as tin oxide and indium oxide to be used in an ITO substrate and an NESA substrate; and organic conductive resins such as polythiophene and polypyrrole. A conductive substance having a work function smaller than 4 eV is suitably used in the cathode of the device. Examples of an available conductive substance include, but not limited to, magnesium, calcium, tin, lead, titanium, yttrium, lithium, ruthenium, manganese, aluminum, and lithium fluoride, and alloys of them. Representative examples of the alloys include, but not limited to, a magnesium/silver alloy, a magnesium/indium alloy, and a lithium/aluminum alloy. A ratio between the components of an alloy is controlled depending on, for example, the temperature of a deposition source, an atmosphere, and the degree of vacuum, and is selected to be an appropriate ratio. Each of the anode and the cathode may be formed of a layer constitution having two or more layers if needed.

At least one surface of the organic EL device of the present invention is desirably sufficiently transparent in the luminous wavelength region of the device so that the device can efficiently emit light. A substrate is also desirably transparent. A transparent electrode is formed by means of any one of the above conductive materials, and is set by means of a method such as deposition or sputtering in such a manner that desired translucency is secured. The light transmittance of an electrode on a light-emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, and polypropylene.

Any one of: dry film forming methods such as vacuum deposition, sputtering, plasma, and ion plating; and wet film forming methods such as spin coating, dipping, and flow coating is applicable to the formation of each layer of the organic EL device according to the present invention. The thickness of each layer is not particularly limited, but must be set to an appropriate thickness. An excessively thick thickness requires an increased applied voltage for obtaining certain optical output, thereby resulting in poor efficiency. An excessively thin thickness causes a pin hole or the like, so sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an available resin include: insulating resins such as polystyrene, polycarbonate, polyallylate, polyester, polyamide, polyurethane, polysulfone, polymethyl methacrylate, polymethyl acrylate, and cellulose, and copolymers of them; photoconductive resins such as poly-N-vinylcarbazole and polysilane; and conductive resins such as polythiophene and polypyrrole. Examples of the additive include an antioxidant, a UV (ultra violet) absorber, and a plasticizer.

The organic EL device of the present invention can find use in applications including: a flat luminous body such as the flat panel display of a wall hanging television; a light source for the backlight, meters, or the like of a copying machine, a printer, or a liquid crystal display; a display panel; and a signal lamp. In addition, the material of the present invention can be used in not only the field of an organic EL device but also the fields of an electrophotographic photosensitive member, a photoelectric transfer element, a solar cell, and an image sensor.

EXAMPLES

Next, the present invention will be described in more detail by way of examples. However, the present invention is not limited to these examples.

Synthesis Example 1 (Synthesis of Compound (2))

Compound (2) was synthesized via the following reaction path.

[Formula 12]

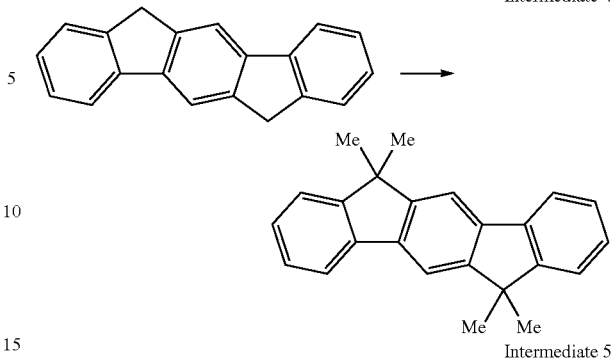
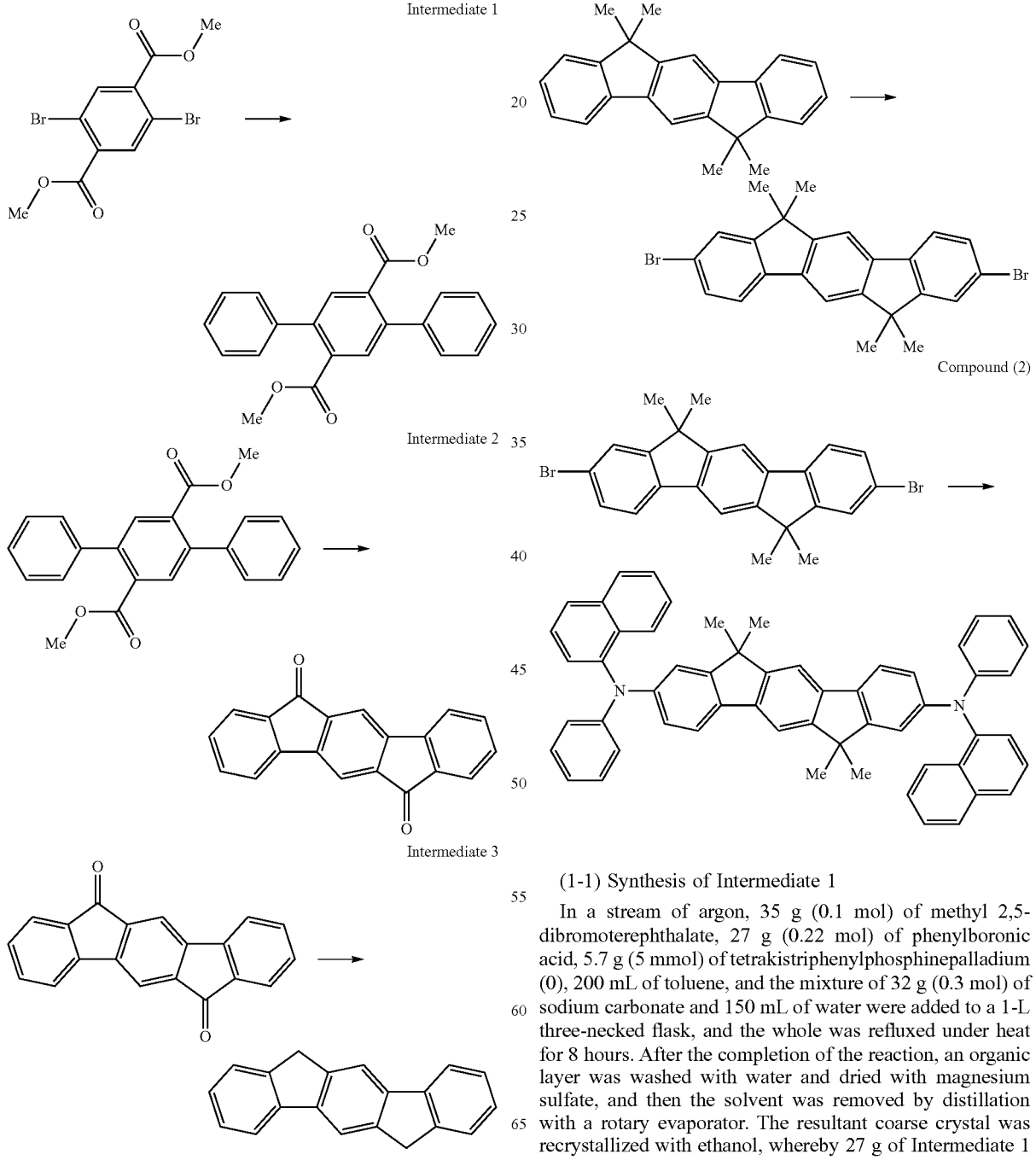

(1-1) Synthesis of Intermediate 1

In a stream of argon, 35 g (0.1 mol) of methyl 2,5-dibromoterephthalate, 27 g (0.22 mol) of phenylboronic acid, 5.7 g (5 mmol) of tetrakistriphenylphosphinepalladium (0), 200 mL of toluene, and the mixture of 32 g (0.3 mol) of sodium carbonate and 150 mL of water were added to a 1-L three-necked flask, and the whole was refluxed under heat for 8 hours. After the completion of the reaction, an organic layer was washed with water and dried with magnesium sulfate, and then the solvent was removed by distillation with a rotary evaporator. The resultant coarse crystal was recrystallized with ethanol, whereby 27 g of Intermediate 1 (white crystal, 80% yield) as a target were obtained.

(1-2) Synthesis of Intermediate 2

Seventeen gram (0.05 mol) of Intermediate 1 and 200 mL of 80% sulfuric acid were added to a 1-L flask, and the whole was stirred under heat at 180° C. for 3 hours. After the completion of the reaction, sulfuric acid was separated, and methylene chloride was added to the remainder. Then, the resultant was washed with an aqueous solution of sodium hydrogen carbonate. After the washed product had been dried with magnesium sulfate, the solvent was removed by distillation with a rotary evaporator, whereby a coarse reaction product was obtained. The product was purified by means of column chromatography (silica gel (hexane solvent): ethyl acetate=95:5), whereby 10 g of Intermediate 2 (gray crystal, 70% yield) as a target were obtained.

(1-3) Synthesis of Intermediate 3

Ten gram (0.035 mol) of Intermediate 2, 8.8 mL (0.175 mol) of hydrazine monohydrate, and 300 mL of diethylene glycol were added to a 1-L flask, and the whole was stirred under heat at 200° C. for 2 hours. After the completion of the reaction, water was added to the resultant, and the precipitate was separated by filtration. The coarse reaction product was reprecipitated with hexane and chloroform, whereby 4.5 g of Intermediate 3 (tan solid, 50% yield) as a target were obtained.

(1-4) Synthesis of Intermediate 4

In a stream of argon, 4 g (0.015 mol) of Intermediate 3, 9 g (0.08 mol) of t-butoxypotassium, and 100 mL of dimethyl sulfoxide (DMSO) were added to a 300-mL three-necked flask, and the reaction system was cooled to 5° C. Subsequently, 11 g (0.08 mol) of methyl iodide were slowly dropped to the resultant, and then the whole was stirred overnight. After the completion of the reaction, water was added to the resultant, and an organic layer was extracted with ethyl acetate and washed with a saturated salt solution. After the washed product had been dried with magnesium sulfate, the solvent was removed by distillation with a rotary evaporator, whereby a coarse reaction product was obtained. The product was purified by means of column chromatography (silica gel (hexane solvent): ethyl acetate=95:5), whereby 4.6 g of Intermediate 4 (white crystal, 95% yield) as a target were obtained.

(1-5) Synthesis of Intermediate 5

Three point one gram (10 mmol) of Intermediate 4 and 20 mL of chloroform were added to a 200-mL flask. Subsequently, 3.2 g (20 mmol) of bromine were slowly dropped to the resultant, and the whole was stirred at room temperature for 2 hours. After the completion of the reaction, an aqueous solution of sodium thiosulfate was added to the reaction liquid, and an organic layer was separated and washed with water and a saturated salt solution. After the washed product had been dried with sodium sulfate, the solvent was removed by distillation with a rotary evaporator. The resultant coarse crystal was recrystallized with ethanol, whereby 3.7 g of Intermediate 5 (white crystal, 80% yield) as a target were obtained.

(1-6) Synthesis of Compound (2)

In a stream of argon, 4.7 g (10 mmol) of Intermediate 5, 5.5 g (25 mmol) of N-phenylnaphthalen-1-amine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 6.7 g of a pale yellow powder were obtained. The resultant compound was identified as Compound (2) (90% yield) because the measurement of the field desorption mass spectrum (FD-MS) of the compound resulted in m/Z=744 for $C_{56}H_{44}N_2$=744.

Synthesis Example 2 (Synthesis of Compound (14))

Compound (14) was synthesized via the following reaction path.

[Formula 13]

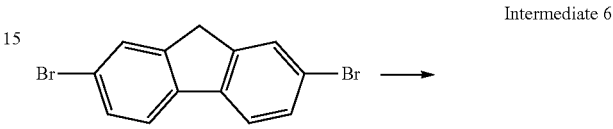

Intermediate 6

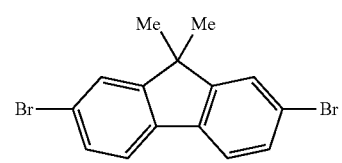

Intermediate 7

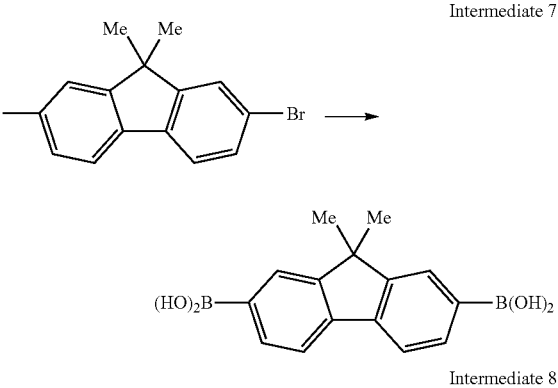

Intermediate 8

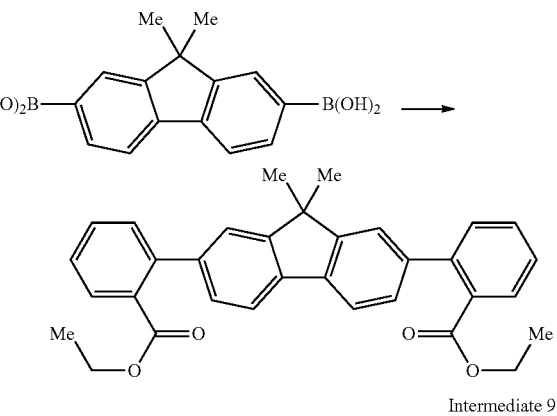

Intermediate 9

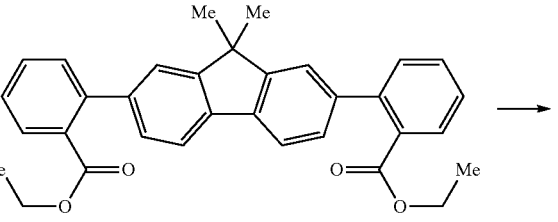

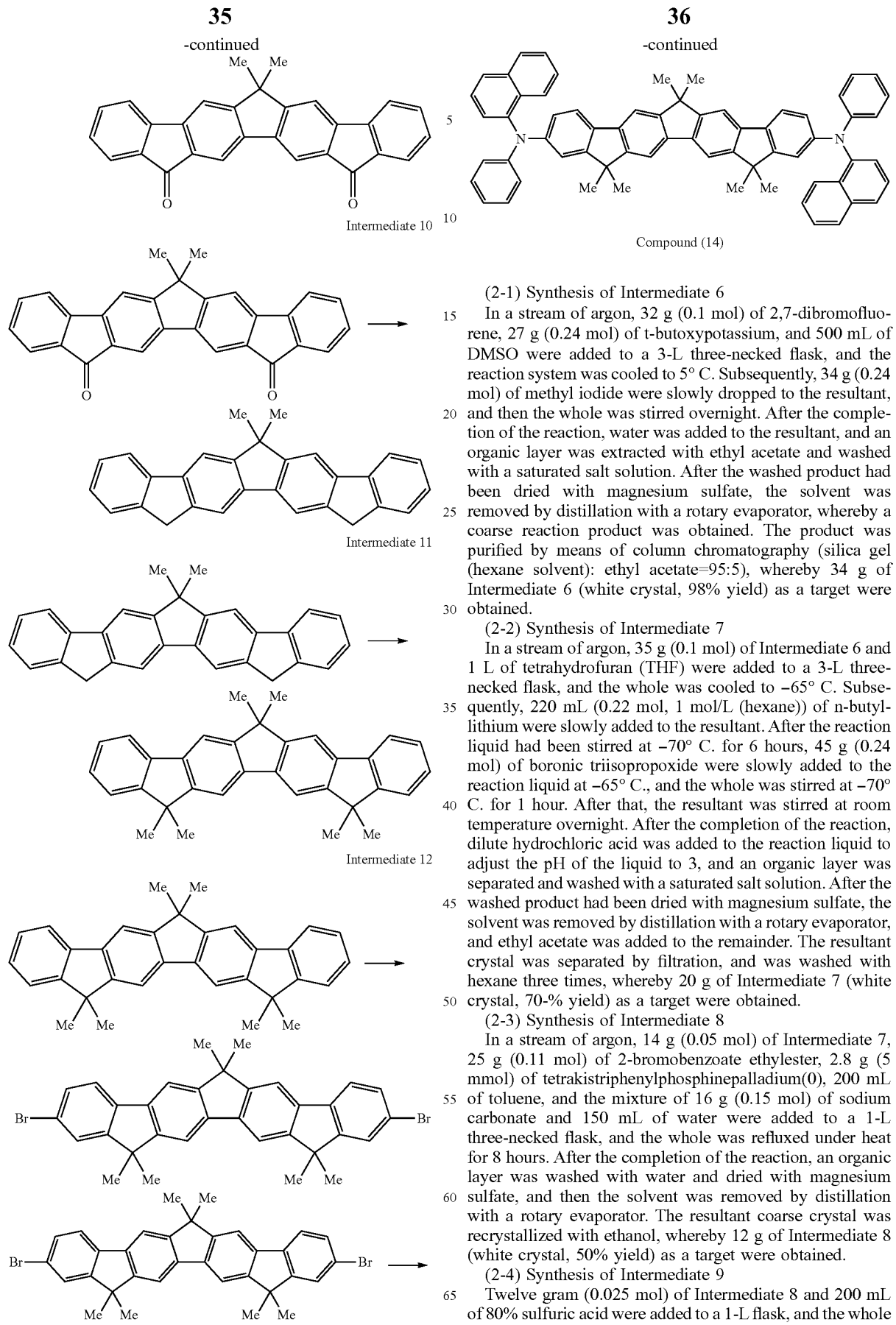

Compound (14)

(2-1) Synthesis of Intermediate 6

In a stream of argon, 32 g (0.1 mol) of 2,7-dibromofluorene, 27 g (0.24 mol) of t-butoxypotassium, and 500 mL of DMSO were added to a 3-L three-necked flask, and the reaction system was cooled to 5° C. Subsequently, 34 g (0.24 mol) of methyl iodide were slowly dropped to the resultant, and then the whole was stirred overnight. After the completion of the reaction, water was added to the resultant, and an organic layer was extracted with ethyl acetate and washed with a saturated salt solution. After the washed product had been dried with magnesium sulfate, the solvent was removed by distillation with a rotary evaporator, whereby a coarse reaction product was obtained. The product was purified by means of column chromatography (silica gel (hexane solvent): ethyl acetate=95:5), whereby 34 g of Intermediate 6 (white crystal, 98% yield) as a target were obtained.

(2-2) Synthesis of Intermediate 7

In a stream of argon, 35 g (0.1 mol) of Intermediate 6 and 1 L of tetrahydrofuran (THF) were added to a 3-L three-necked flask, and the whole was cooled to −65° C. Subsequently, 220 mL (0.22 mol, 1 mol/L (hexane)) of n-butyllithium were slowly added to the resultant. After the reaction liquid had been stirred at −70° C. for 6 hours, 45 g (0.24 mol) of boronic triisopropoxide were slowly added to the reaction liquid at −65° C., and the whole was stirred at −70° C. for 1 hour. After that, the resultant was stirred at room temperature overnight. After the completion of the reaction, dilute hydrochloric acid was added to the reaction liquid to adjust the pH of the liquid to 3, and an organic layer was separated and washed with a saturated salt solution. After the washed product had been dried with magnesium sulfate, the solvent was removed by distillation with a rotary evaporator, and ethyl acetate was added to the remainder. The resultant crystal was separated by filtration, and was washed with hexane three times, whereby 20 g of Intermediate 7 (white crystal, 70-% yield) as a target were obtained.

(2-3) Synthesis of Intermediate 8

In a stream of argon, 14 g (0.05 mol) of Intermediate 7, 25 g (0.11 mol) of 2-bromobenzoate ethylester, 2.8 g (5 mmol) of tetrakistriphenylphosphinepalladium(0), 200 mL of toluene, and the mixture of 16 g (0.15 mol) of sodium carbonate and 150 mL of water were added to a 1-L three-necked flask, and the whole was refluxed under heat for 8 hours. After the completion of the reaction, an organic layer was washed with water and dried with magnesium sulfate, and then the solvent was removed by distillation with a rotary evaporator. The resultant coarse crystal was recrystallized with ethanol, whereby 12 g of Intermediate 8 (white crystal, 50% yield) as a target were obtained.

(2-4) Synthesis of Intermediate 9

Twelve gram (0.025 mol) of Intermediate 8 and 200 mL of 80% sulfuric acid were added to a 1-L flask, and the whole was stirred under heat at 180° C. for 3 hours. After the completion of the reaction, sulfuric acid was separated, and methylene chloride was added to the remainder. Then, the resultant was washed with an aqueous solution of sodium hydrogen carbonate. After the washed product had been dried with magnesium sulfate, the solvent was removed by distillation with a rotary evaporator, whereby a coarse reaction product was obtained. The product was purified by means of column chromatography (silica gel (hexane solvent): ethyl acetate=95:5), whereby 6.2 g of Intermediate 9 (gray crystal, 60% yield) as a target were obtained.

(2-5) Synthesis of Intermediate 10

Six gram (0.015 mol) of Intermediate 9, 4 mL (0.075 mol) of hydrazine monohydrate, and 100 mL of diethylene glycol were added to a 500-mL flask, and the whole was stirred under heat at 200° C. for 2 hours. After the completion of the reaction, water was added to the resultant, and the precipitate was separated by filtration. The coarse reaction product was reprecipitated with hexane and chloroform, whereby 2.9 g of Intermediate 10 (tan solid, 50% yield) as a target were obtained.

(2-6) Synthesis of Intermediate 11

In a stream of argon, 2.9 g (7.5 mol) of Intermediate 10, 3.8 g (40 mol) of t-butoxypotassium, and 100 mL of DMSO were added to a 300-mL three-necked flask, and the reaction system was cooled to 5° C. Subsequently, 5.6 g (40 mol) of methyl iodide were slowly dropped to the resultant, and then the whole was stirred overnight. After the completion of the reaction, water was added to the resultant, and an organic layer was extracted with ethyl acetate and washed with a saturated salt solution. After the washed product had been dried with magnesium sulfate, the solvent was removed by distillation with a rotary evaporator, whereby a coarse reaction product was obtained. The product was purified by means of column chromatography (silica gel (hexane solvent): ethyl acetate=95:5), whereby 3.0 g of Intermediate 11 (white crystal, 90% yield) as a target were obtained.

(2-7) Synthesis of Intermediate 12

Two point two gram (5 mmol) of Intermediate 11 and 20 mL of chloroform were added to a 200-mL flask. Subsequently, 1.6 g (10 mmol) of bromine were slowly dropped to the resultant, and the whole was stirred at room temperature for 2 hours. After the completion of the reaction, an aqueous solution of sodium thiosulfate was added to the reaction liquid, and an organic layer was separated and washed with water and a saturated salt solution. After the washed product had been dried with sodium sulfate, the solvent was removed by distillation with a rotary evaporator. The resultant coarse crystal was recrystallized with ethanol, whereby 2.1 g of Intermediate 12 (white crystal, 70% yield) as a target were obtained.

(2-8) Synthesis of Compound (14)

In a stream of argon, 6.0 g (10 mmol) of Intermediate 12, 5.5 g (25 mmol) of N-phenylnaphthalen-1-amine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 7.3 g of a pale yellow powder were obtained. The resultant compound was identified as Compound (14) (85% yield) because the measurement of FD-MS of the compound resulted in m/Z=860 for $C_{65}H_{52}N=860$.

Synthesis Example 3 (Synthesis of Compound (5))

In a stream of argon, 4.7 g (10 mmol) of Intermediate 5, 6.7 g (25 mmol) of bis(2-naphthyl)amine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 6.7 g of a pale yellow powder were obtained (80% yield). The $^1$H-NMR spectrum and FD-MS spectrum of the resultant compound were measured, whereby the compound was identified as Compound (5). It should be noted that the $^1$H-NMR spectrum (see the FIGURE and Table 1) was measured with a DRX-500 (heavy methylene chloride solvent) manufactured by Brucker. In addition, the maximum absorption wavelength and maximum fluorescent wavelength of the resultant compound measured in a toluene solution were 410 nm and 428 nm, respectively.

TABLE 1

| Peak No. | Position (ppm) | Height (%) |
|---|---|---|
| 1 | 0.08 | 71.55 |
| 2 | 1.26 | 15.86 |
| 3 | 2.06 | 13.96 |
| 4 | 2.12 | 77.87 |
| 5 | 2.34 | 11.48 |
| 6 | 7.13 | 23.07 |
| 7 | 7.15 | 23.61 |
| 8 | 7.31 | 39.56 |
| 9 | 7.36 | 22.93 |
| 10 | 7.37 | 45.22 |
| 11 | 7.38 | 51.93 |
| 12 | 7.39 | 87.14 |
| 13 | 7.39 | 81.02 |
| 14 | 7.39 | 62.22 |
| 15 | 7.40 | 54.30 |
| 16 | 7.40 | 77.62 |
| 17 | 7.42 | 29.66 |
| 18 | 7.52 | 63.93 |
| 19 | 7.59 | 49.00 |
| 20 | 7.61 | 43.63 |
| 21 | 7.66 | 36.06 |
| 22 | 7.68 | 34.43 |
| 23 | 7.70 | 74.43 |
| 24 | 7.77 | 64.64 |
| 25 | 7.79 | 100.00 |
| 26 | 7.81 | 48.39 |

Example 1 (Production of Organic EL Device)

(1) Production of Organic EL Device

A transparent electrode composed of an indium tin oxide having a thickness of 130 nm was arranged on a glass substrate measuring 25×75×1.1 mm. The glass substrate was subjected to ultrasonic cleaning in isopropyl alcohol, and was irradiated with ultraviolet light and ozone for cleaning.

Next, the glass substrate equipped with the transparent electrode was mounted on a substrate holder in the deposition tank of a vacuum deposition device. In addition, the degree of vacuum in a vacuum tank was reduced to $1\times10^{-3}$ Pa. After that, a hole-injecting layer, a hole-transporting layer, a light-emitting layer, an electron-transporting layer, an electron-injecting layer, and a cathode layer were sequentially laminated on an anode (transparent electrode) layer under the following deposition conditions, whereby an organic EL device was produced.

Hole-injecting layer: (material) N',N''-bis[4-(diphenylamino)phenyl]-N',N''-diphenylbiphenyl-4,4'-diamine; deposition condition 2 nm/sec; thickness 60 nm Hole-transporting layer: (material) the Compound (2); deposition condition 2 nm/sec; thickness 20 nm Light-emitting layer: 10-(4-(naphthylen-1-yl)phenyl)-9-(naphthylen-3-yl)anthracene as a host material; deposition condition 2 nm/sec and tetrakis(2-naphtyl)-4,4'-diaminostilbene as a dopant; deposition condition 0.2 nm/sec are simultaneously deposited from the vapor; thickness 40 nm (weight ratio between the host material and the dopant is 40:2)

Electron-transporting layer: (material) tris(8-hydroxyquinolino)aluminum; deposition condition 2 nm/sec; thickness 20 nm Electron-injecting layer: (material) lithium fluoride; deposition condition 0.1 nm/sec; thickness 1 nm Cathode layer: (material) aluminum; deposition condition 2 nm/sec; thickness 200 nm (2) Evaluation of Organic EL Device The resultant device was subjected to an energization test. As a result, it was confirmed that emission luminance was 500 cd/m² at a voltage of 6.5 V and a luminescent color was blue. In addition, when the device was driven at a constant current with initial emission luminance set to 500 cd/m², a time period required for the luminance to reduce by 10% was 100 hours. Table 2 shows the obtained results. When the device was stored at 85° C. for 500 hours, no change in driving voltage was observed.

Examples 2 to 5 (Production of Organic EL Device)

In each of the examples, an organic EL device was produced in the same manner as in Example 1 except that a material described in Table 2 was used instead of Compound (2) as a material for hole-transporting layer.

Each of the resultant devices was evaluated in the same manner as in Example 1. As a result, as shown in Table 2, blue light emission was observed in each of all the devices. In addition, emission luminance was 450 to 510 cd/m², and a time period required for the luminance to reduce by 10% was 90 to 110 hours. When each of those devices was stored at 85° C. for 500 hours, no change in driving voltage was observed.

Comparative Examples 1 to 3 (Production of Organic EL Devices)

Organic EL devices were each produced in the same manner as in Example 1 except that any one of the following materials was used as a material for a hole transporting layer instead of Compound (2).

Comparative Example 1: Compound (A) N,N'-bis(3-methylphenyl)-N,N'-bis(phenyl)benzidine Comparative Example 2: Compound (B) N,N'-di(naphthalen-1-yl)-N,N'-diphenylbenzidine Comparative Example 3: Compound (C) 4,4-bis(N,N-diphenylamino)-terphenyl Each of the resultant devices was evaluated in the same manner as in Example 1. As a result, as shown in Table 2, each of all the devices was observed to emit blue light, showed an emission luminance of 380 to 430 cd/m², and had a time period required for the luminance to reduce by 10% of 50 to 60 hours. In addition, those devices were stored at 85° C. for 500 hours. As a result, the voltage at which each of the devices was driven changed by 1 V or more.

TABLE 2

| | Hole transporting material | Voltage at which device is driven (V) | Luminescent color | Emission luminance (cd/m²) | Time period required for luminance to reduce by 10% (hours) | Voltage change after storage at 85° C. (500 hours) |
|---|---|---|---|---|---|---|
| Example 1 | (2) | 6.5 | Blue | 500 | 100 | No change |
| Example 2 | (6) | 6.5 | Blue | 510 | 110 | No change |
| Example 3 | (14) | 6.5 | Blue | 490 | 90 | No change |
| Example 4 | (32) | 6.5 | Blue | 480 | 100 | No change |
| Example 5 | (38) | 6.5 | Blue | 450 | 90 | No change |
| Comparative Example 1 | (A) | 6.5 | Blue | 400 | 50 | 1 V |
| Comparative Example 2 | (B) | 6.5 | Blue | 430 | 60 | 1 V |
| Comparative Example 3 | (C) | 6.5 | Blue | 380 | 50 | 2 V |

Example 6 (Production of Organic EL Device)

(1) Production of Organic EL Device

A transparent electrode composed of an indium tin oxide having a thickness of 130 nm was arranged on a glass substrate measuring 25×75×1.1 mm. The glass substrate was subjected to ultrasonic cleaning in isopropyl alcohol, and was irradiated with ultraviolet light and ozone for cleaning.

Next, the glass substrate equipped with the transparent electrode was mounted on a substrate holder in the deposition tank of a vacuum deposition device. In addition, the degree of vacuum in a vacuum tank was reduced to $1 \times 10^{-3}$ Pa. After that, a hole-injecting layer, a hole-transporting layer, a light-emitting layer, an electron-transporting layer, an electron-injecting layer, and a cathode layer were sequentially laminated on an anode (transparent electrode) layer under the following deposition conditions, whereby an organic EL device was produced.

Hole-injecting layer: (material) N',N''-bis[4-(diphenylamino)phenyl]-N',N''-diphenylbiphenyl-4,4'-diamine; deposition condition 2 nm/sec; thickness 60 nm Hole-transporting layer: (material) N,N,N',N'-tetrakis(4-biphenyl)-4,4'-benzidine; deposition condition 2 nm/sec; thickness 20 nm Light-emitting layer: 10-(4-(naphthylen-1-yl)phenyl)-9-(naphthylen-3-yl)anthracene as a host material; deposition condition 2 nm/sec and the above compound (33) as a dopant; deposition condition 0.1 nm/sec are simultaneously deposited from the vapor; thickness 40 nm (weight ratio between the host material and the dopant is 40:2)

Electron-transporting layer: (material) tris(8-hydroxyquinolino)aluminum; deposition condition 2 nm/sec; thickness 20 nm Electron-injecting layer: (material) lithium fluoride; deposition condition 0.1 nm/sec; thickness 1 nm Cathode layer: (material) aluminum; deposition condition 2 nm/sec; thickness 200 nm (2) Evaluation of Organic EL Device The resultant device was subjected to an energization test. As a result, it was confirmed that emission luminance was 900 cd/m² at a voltage of 6.5 V and a luminescent color was blue. In addition, when the device was driven at a constant current with initial emission luminance set to 2,000 cd/m², a time period required for the luminance to reduce by 50% was 3,000 hours. When the device was stored at 85° C. for 500 hours, no change in driving voltage was observed.

Comparative Example 4 (Production of Organic EL Device)

An organic EL device was produced in the same manner as in Example 6 except that 1,6-bis(diphenylamino)pyrene was used as a material for a light emitting layer instead of Compound (33) in Example 6.

The resultant device was evaluated in the same manner as in Example 1. As a result, the device was observed to emit blue light, showed an emission luminance of 800 cd/m², and had a time period required for the luminance to reduce by 50% as short as 500 hours. In addition, the device was stored at 85° C. for 500 hours. As a result, the voltage at which the device was driven showed no change.

Therefore, the use of the aromatic amine derivative of the present invention as a dopant for a light-emitting layer significantly improves a half life.

INDUSTRIAL APPLICABILITY

As described above in detail, each of the aromatic amine derivative of the present invention and the organic EL device using the derivative has high emission luminance, high heat resistance, excellent high-temperature storage stability, and a long lifetime. Therefore, each of them can be highly practically used in, for example, an on-vehicle device, and is useful.

The invention claimed is:

1. An organic electroluminescence device, comprising:
a cathode;
an anode; and
an organic thin film layer comprising one or more layers, wherein
the organic thin film layer comprises a light emitting layer,
the organic thin film layer is interposed between the cathode and the anode,
the organic thin film layer comprises a hole transporting layer between the anode and the light emitting layer, and
the hole transporting layer comprises an aromatic amine compound represented by formula (2-a):

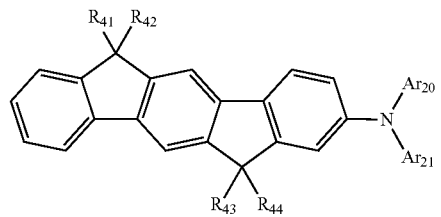

(2-a)

wherein:
each of $Ar_{20}$ and $Ar_{21}$ independently represents a substituted or unsubstituted aryl group having 5 to 40 ring carbon atoms or a substituted or unsubstituted heterocyclic group having 5 to 40 ring atoms, provided that each of $Ar_{20}$ and $Ar_{21}$ does not contain a vinyl group;
each of $R_{41}$ to $R_{44}$ independently represents a hydrogen atom, an unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, an unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, a substituted or unsubstituted silyl group, a halogen atom, a cyano group, a nitro group, a hydroxyl group, or a carboxyl group;
a leftmost benzene ring is optionally substituted by 1 to 3 substituents selected from the group consisting of a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, a substituted or unsubstituted silyl group, a halogen atom, a cyano group, a nitro group, a hydroxyl group, and a carboxyl group; and
when the leftmost benzene ring is substituted by 2 or 3 substituents, the 2 or 3 substituents are different from each other.

2. The organic electroluminescence device according to claim 1, wherein each of $Ar_{20}$ and $Ar_{21}$ is independently selected from the group consisting of a phenyl group, a naphthyl group, a biphenyl group, an anthranyl group, a phenanthryl group, a pyridinyl group, a pyrenyl group, a chrysenyl group, a fluoranthenyl group, and a fluorenyl group, each optionally substituted.

3. The organic electroluminescence device according to claim 1, wherein the aryl group having 5 to 40 ring carbon atoms for $Ar_{20}$ and $Ar_{21}$ is optionally substituted by an aryl group, an alkyl group, an alkoxy group, an aralkyl group, an aryloxy group, an arylthio group, or an alkoxycarbonyl group.

4. The organic electroluminescence device according to claim 1, wherein each of $R_{41}$ to $R_{44}$ independently represents a hydrogen atom, an unsubstituted aryl group having 5 to 50 ring carbon atoms or an unsubstituted alkyl group having 1 to 50 carbon atoms.

5. The organic electroluminescence device according to claim 4, wherein the aryl group represented by each of $R_{41}$ to $R_{44}$ is selected from the group consisting of a phenyl group, a naphthyl group, a biphenyl group, an anthranyl group, a phenanthryl group, a pyrenyl group, a chrysenyl group, a fluoranthenyl group, and a fluorenyl group.

6. The organic electroluminescence device according to claim 4, wherein the alkyl group represented by each of $R_{41}$ to $R_{44}$ is selected from the group consisting of a methyl group, an ethyl group, a propyl group, an isopropyl group, a n-butyl group, a s-butyl group, an isobutyl group, a t-butyl group, a n-pentyl group, a n-hexyl group, a n-heptyl group, and a n-octyl group.

7. The organic electroluminescence device according to claim 1, wherein the optional substituent of the leftmost benzene ring is selected from the group consisting of a methyl group, an ethyl group, a t-butyl group, a phenyl group, a 1-naphthyl group, and a 2-naphthyl group.

8. The organic electroluminescence device according to claim 1, wherein the compound is represented by any of formulae (30) to (34):

(30)

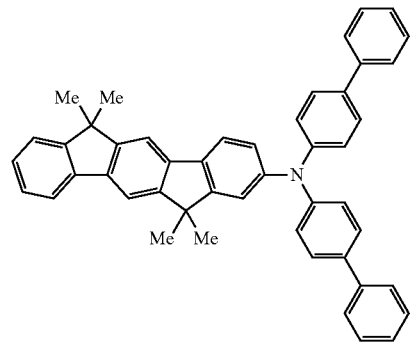

(31)

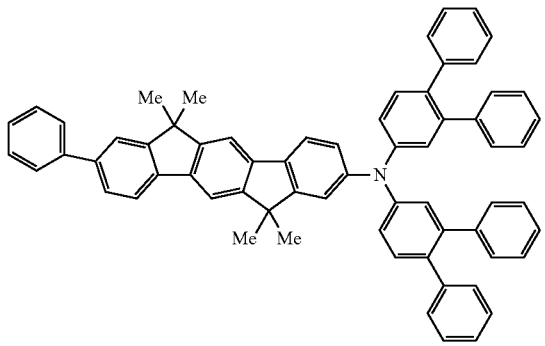

(32)

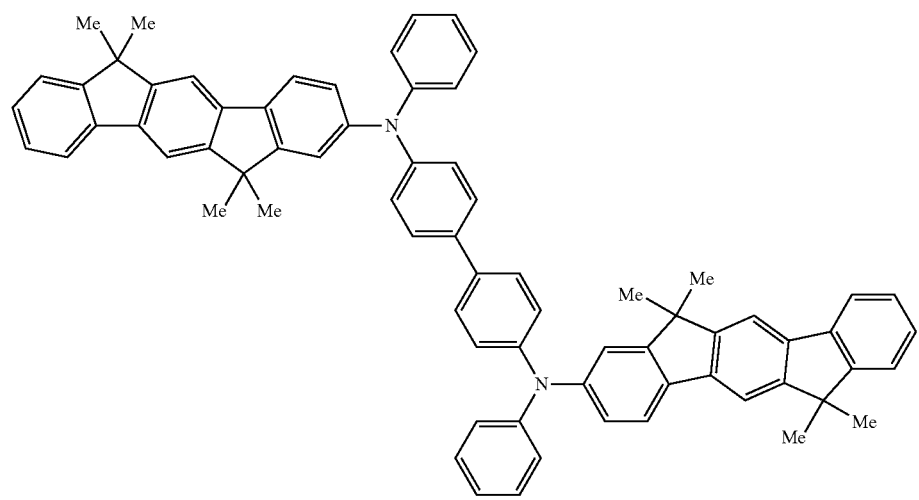

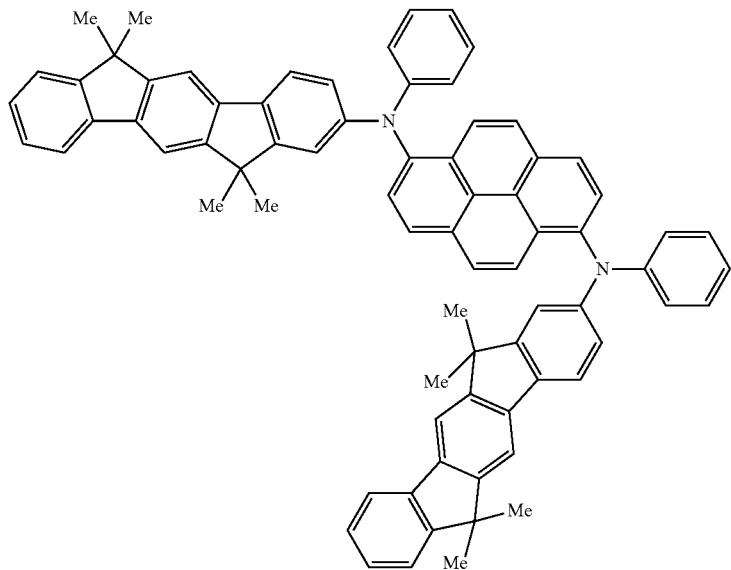

(33)

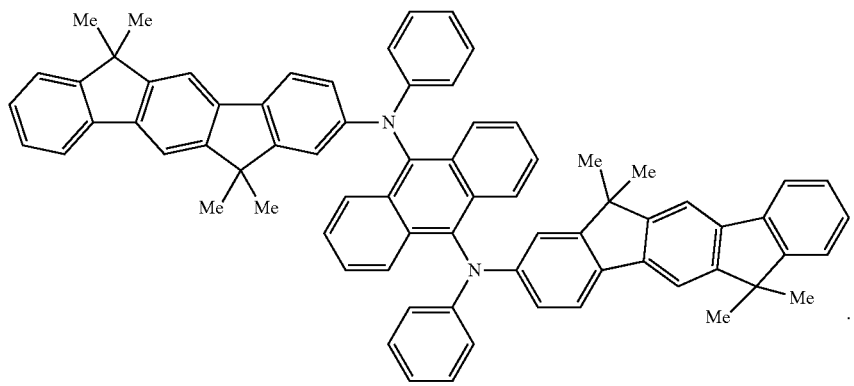

(34)

9. The organic electroluminescence device according to claim 1, wherein each of $Ar_{20}$ and $Ar_{21}$ independently represents a substituted or unsubstituted aryl group having 5 to 40 ring carbon atoms, provided that each of $Ar_{20}$ and $Ar_{21}$ does not contain a vinyl group.

10. The organic electroluminescence device according to claim 1, wherein each of $Ar_{20}$ and $Ar_{21}$ independently represents a substituted or unsubstituted heterocyclic group having 5 to 40 ring atoms, provided that each of $Ar_{20}$ and $Ar_{21}$ does not contain a vinyl group.

11. The organic electroluminescence device according to claim 1, wherein the leftmost benzene ring is unsubstituted.

12. The organic electroluminescence device according to claim 1, wherein the leftmost benzene ring is substituted by 1 to 3 substituents selected from the group consisting of a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, a substituted or unsubstituted silyl group, a halogen atom, a cyano group, a nitro group, a hydroxyl group, and a carboxyl group.

13. The organic electroluminescence device according to claim 1, wherein each of $R_{41}$ to $R_{44}$ independently represents a substituted or unsubstituted alkyl group having 1 to 50 carbon atoms.

14. The organic electroluminescence device according to claim 1, wherein each of $R_{41}$ to $R_{44}$ are methyl groups.

15. The organic electroluminescence device according to claim 1, wherein
    each of $Ar_{20}$ and $Ar_{21}$ independently represents a substituted or unsubstituted aryl group having 5 to 40 ring carbon atoms, provided that each of $Ar_{20}$ and $Ar_{21}$ does not contain a vinyl group;
    each of $R_{41}$ to $R_{44}$ independently represents a hydrogen atom, an unsubstituted aryl group having 5 to 50 ring carbon atoms, or a substituted or unsubstituted alkyl group having 1 to 50 carbon atoms; and
    the leftmost benzene ring is optionally substituted by a substituted or unsubstituted aryl group having 5 to 50 ring carbon atoms, or a substituted or unsubstituted alkyl group having 1 to 50 carbon atoms.

16. The organic electroluminescence device according to claim 1, wherein the leftmost benzene ring is optionally substituted by one substituent.

17. The organic electroluminescence device according to claim 1, wherein each of $Ar_{20}$ and $Ar_{21}$ independently represents a substituted or unsubstituted aryl group having 5 to 40 ring carbon atoms or a substituted or unsubstituted heterocyclic group having 5 to 40 ring atoms, provided that each of $Ar_{20}$ and $Ar_{21}$ does not contain a vinyl group;

each of $R_{41}$ to $R_{44}$ independently represents a hydrogen atom, an unsubstituted aryl group having 5 to 50 ring carbon atoms, or a substituted or unsubstituted alkyl group having 1 to 50 carbon atoms; and a leftmost benzene ring is optionally substituted by 1 to 3 substituents selected from the group consisting of a substituted or unsubstituted aryl group having 5 to 50 ring carbon atoms and a substituted or unsubstituted alkyl group having 1 to 50 carbon atoms.

18. The organic electroluminescence device according to claim 1, wherein each of $Ar_{20}$ and $Ar_{21}$ independently represents a substituted or unsubstituted aryl group having 5 to 40 ring carbon atoms or a substituted or unsubstituted heterocyclic group having 5 to 40 ring atoms, provided that each of $Ar_{20}$ and $Ar_{21}$ does not contain a vinyl group;

each of $R_{41}$ to $R_{44}$ independently represents a substituted or unsubstituted alkyl group having 1 to 50 carbon atoms; and a leftmost benzene ring is unsubstituted.

19. The organic electroluminescence device according to claim 1, wherein the organic electroluminescence device is a blue emitting device.

\* \* \* \* \*